(12) United States Patent
Bone et al.

(10) Patent No.: US 8,815,590 B2
(45) Date of Patent: Aug. 26, 2014

(54) COMPOSITION AND METHOD FOR DIFFERENTIATION OF HUMAN EMBRYONIC STEM CELLS

(75) Inventors: Heather K. Bone, Winterbourne (GB); David Tosh, Bath (GB); Melanie J. Welham, Whitley (GB)

(73) Assignee: Stem Cells for Safer Medicines Limited (GB)

( * ) Notice: Subject to any disclaimer, the term of this patent is extended or adjusted under 35 U.S.C. 154(b) by 0 days.

(21) Appl. No.: 13/512,240

(22) PCT Filed: Nov. 26, 2010

(86) PCT No.: PCT/GB2010/002184
§ 371 (c)(1),
(2), (4) Date: Oct. 15, 2012

(87) PCT Pub. No.: WO2011/064549
PCT Pub. Date: Jun. 3, 2011

(65) Prior Publication Data
US 2013/0028872 A1    Jan. 31, 2013

(30) Foreign Application Priority Data

Nov. 27, 2009 (GB) .................................. 0920865.3
Feb. 11, 2010 (GB) .................................. 1002329.9

(51) Int. Cl.
*C12N 5/00*    (2006.01)

(52) U.S. Cl.
USPC ........................................ 435/377; 435/325

(58) Field of Classification Search
USPC ................................................ 435/377, 325
See application file for complete search history.

(56) References Cited

U.S. PATENT DOCUMENTS

2003/0003573 A1    1/2003    Rambhatle et al.

FOREIGN PATENT DOCUMENTS

| WO | WO2009018453 | 2/2009 | |
|----|----|----|----|
| WO | WO2009132068 | 10/2009 | |
| WO | WO 2009/154606 A1 * | 12/2009 | ............. C12N 15/09 |

OTHER PUBLICATIONS

Yamada et al. Stem Cells 20:146-154, 2002.*
Agarwal et al., "Efficient Differentiation of Functional Hepatocytes from Human Embryonic Stem Cells," Stem Cells, 26:1117-1127 (2008).
Baharvand et al., "Differentiation of Human Embryonic Stem Cells into Hepatocytes in 2D and 3D Culture Systems in vitro," Int. J. Dev. Biol., 50:645-652 (2006).
Bone et al., "Involvement of GSK-3 in Regulation of Murine Embryonic Stem Cell Self-Renewal by a Series of Bisindolylmaleimides," Chemistry & Biology, 16:15-27 (2009).
Bone et al., "A Novel Chemically Directed Route for the Generation of Definitive Endoderm from Human Embryonic Stem Cells Based on Inhibition of GSK-3," Journal of Cell Science, 124: 1992-2000 (2011).
Hay et al., "Highly Efficient Differentiation of hESCs to Functional Hepatic Endoderm Requires ActivinA and Wnt3a Signaling," PNAS, 105: 12301-12306 (2008).
Sato et al., "Maintenance of Pluripotency in Human and Mouse Embryonic Stem Cells Through Activation of Wnt Signaling by a Pharmacological GSK-3-Specific Inhibitor," Nature Medicine, 10:55-63 (2004).
International Search Report dated Jul. 12, 2011 from corresponding PCT Application No. PCT/GB2010/002184.

* cited by examiner

*Primary Examiner* — Marcia S Noble
(74) *Attorney, Agent, or Firm* — McDermott Will & Emery LLP

(57) ABSTRACT

Described are methods for inducing differentiation of a human embryonic stem cell or a population of human embryonic stem cells toward a cell or population of cells characteristic of the definitive endoderm, the method comprising incubating the cell or population of cells with a GSK-3 inhibitor. Also described are methods for inducing differentiation of a cell or population of cells, characteristic of the definitive endoderm, towards a hepatocyte-like cell or a population of hepatocyte-like cells, and methods for inducing differentiation of a human embryonic stem cell or a population of human embryonic stem cells toward a hepatocyte-like cell or a population of hepatocyte-like cells. Further described are cells obtained by the methods and uses thereof in therapy and toxicity screening.

5 Claims, 8 Drawing Sheets

COMPOSITION AND METHOD FOR DIFFERENTIATION OF HUMAN EMBRYONIC STEM CELLS

CROSS REFERENCE TO RELATED APPLICATIONS

This application is the U.S. National Stage of International Application No. PCT/GB2010/002184, filed Nov. 26, 2010 and published in English, which claims the benefit of GB Application No. 0920865.3, filed Nov. 27, 2009, and GB Application No. 1002329.9, filed Feb. 11, 2010.

SEQUENCE LISTING

The instant application contains a Sequence Listing which has been submitted in ASCII format via EFS-Web and is hereby incorporated by reference in its entirety. Said ASCII copy, created on Jan. 9, 2014, is named 090995-0011 sequence listing.txt and is 6,142 bytes in size.

BACKGROUND OF THE INVENTION

The present application relates to compositions and methods for differentiation of human embryonic stem cells, in particular to compositions and methods for differentiation of human embryonic stem cells towards definitive endoderm cells.

Human embryonic stem cells (ESCs) have the remarkable ability of both unlimited self-renewal and the potential to differentiate into all the cells comprising the three germ layers of the developing embryo, making them attractive as a source of cells for use in regenerative medicine and as a model for early human development.

Murine embryonic stem cells can be maintained in a self-renewing state via incubation with glycogen synthase kinase-3 (GSK-3) inhibitors. For example, in Bone et al (2009) a number of GSK-3 inhibitors have been described which are capable of promoting self-renewal of murine embryonic stem cells.

The sequence of events that occur during normal development in vivo are likely to provide important clues to understanding the control of ESC differentiation. The definitive endoderm (DE) arises during the gastrulation stage of early embryogenesis when formation of the primary germ layers, the mesoderm, endoderm and ectoderm, occurs. At this stage, undifferentiated epiblast cells migrate through a structure called the primitive streak (PS). The mesoderm and DE are specified in the anterior region of the PS and are thought to arise from a common progenitor population, the mesendoderm (Tada et al., 2005).

The ability to efficiently generate definitive endoderm, the precursor cell type that gives rise to endoderm-derived cell lineages, including those of the liver pancreas, lungs, thyroid and intestines, is of great clinical importance. In particular, there is a need for derivation of endoderm with hepatic potential from a therapeutic and pharmaceutical perspective. There is a shortage of donor livers available for transplantation therapies. In addition, there is a requirement for functional hepatocytes for use in predictive toxicology. At present, primary human hepatocytes are used for pharmaceutical screening but with the shortage of cells and the inefficient propagation and maintenance of this cell type, an alternative source must be found and human ESC-derived hepatocytes hold great promise.

SUMMARY OF THE INVENTION

According to one aspect of the present invention, there is provided a method for inducing differentiation of a human embryonic stem cell or a population of human embryonic stem cells toward a cell or population of cells characteristic of the definitive endoderm, the method comprising incubating the cell or population of cells with a GSK-3 inhibitor.

Remarkably, it has been found that, in direct contrast to the role of GSK-3 inhibitors in promoting self-renewal of murine embryonic stem cells, when administered to human embryonic stem cells, GSK-3 inhibitors are able to induce differentiation.

According to another aspect of the present invention, there is provided use of a GSK-3 inhibitor for inducing differentiation of a human embryonic stem cell or a population of human embryonic stem cells toward a cell or population of cells characteristic of the definitive endoderm.

According to another aspect of the present invention, there is provided a human embryonic stem cell differentiation composition comprising a GSK-3 inhibitor, wherein the composition is capable of differentiating a human embryonic stem cell or population of human embryonic stem cells towards a cell or population of cells characteristic of the definitive endoderm.

As such, in one embodiment there is provided a human embryonic stem cell towards definitive endoderm cell differentiation composition comprising a GSK-3 inhibitor.

According to another aspect of the present invention, there is provided a method for inducing differentiation of a cell or population of cells, characteristic of the definitive endoderm, towards a hepatocyte-like cell or a population of hepatocyte-like cells, the method comprising incubating the cell or population of cells with a GSK-3 inhibitor.

According to another aspect of the present invention, there is provided use of a GSK-3 inhibitor for inducing differentiation of a cell or population of cells, characteristic of the definitive endoderm, towards a hepatocyte-like cell or a population of hepatocyte-like cells.

According to a further aspect of the present invention, there is provided a definitive endoderm differentiation composition comprising a GSK-3 inhibitor, wherein the composition is capable of differentiating a cell or a population of cells, characteristic of the definitive endoderm, towards a hepatocyte-like cell or a population of hepatocyte-like cells.

As such, in one embodiment there is provided a definitive endoderm towards hepatocyte-like cell differentiation composition comprising a GSK-3 inhibitor.

According to a further aspect of the present invention, there is provided a method for inducing differentiation of a human embryonic stem cell or a population of human embryonic stem cells toward a hepatocyte-like cell or a population of hepatocyte-like cells, the method comprising incubating the cell or population of cells with a GSK-3 inhibitor.

According to another aspect of the present invention, there is provided use of a GSK-3 inhibitor for inducing differentiation of a human embryonic stem cell or a population of human embryonic stem cells toward a hepatocyte-like cell or a population of hepatocyte-like cells.

According to another aspect of the present invention, there is provided a human embryonic stem cell differentiation composition comprising a GSK-3 inhibitor, wherein the composition is capable of differentiating a human embryonic stem cell or population of human embryonic stem cells towards a hepatocyte-like cell or a population of hepatocyte-like cells.

As such, in one embodiment there is provided a human embryonic stem cell towards hepatocyte-like cell differentiation composition comprising a GSK-3 inhibitor.

Preferably the methods are in vitro methods.

In another embodiment of the present invention, there is provided a culture medium comprising a composition as described herein. Examples of preferred culture media include mTeSR1® chemically defined hESC media (from Stem Cell Technologies) and KnockOut (KO) Dulbeco's modified Eagle's medium (DMEM; Invitrogen) supplemented with KO serum replacement.

As such, in one embodiment there is provided a human embryonic stem cell towards definitive endoderm differentiation culture medium comprising a GSK-3 inhibitor.

In another embodiment there is provided a definitive endoderm towards hepatocyte-like cell differentiation culture medium comprising a GSK-3 inhibitor.

In a further embodiment there is provided a human embryonic stem cell towards hepatocyte-like cell differentiation culture medium comprising a GSK-3 inhibitor.

According to a further aspect of the present invention, there is provided a cell or population of cells obtained by a method described herein.

A further aspect of the present invention relates to use of a human embryonic stem cell and a GSK-3 inhibitor in the manufacture of a medicament for the treatment of a liver disease or for the reconstruction of a damaged liver in a subject.

A further aspect of the present invention relates to use of a definitive endoderm cell and a GSK-3 inhibitor in the manufacture of a medicament for the treatment of a liver disease or for the reconstruction of a damaged liver in a subject.

A further aspect of the present invention relates to use of a cell of population of cells as described herein in the manufacture of a medicament for the treatment of a liver disease or for the reconstruction of a damaged liver in a subject.

Another aspect of the present invention relates to a method for treating a liver disease or for the reconstruction of a damaged liver in a subject, the method comprising administering to a subject a composition comprising a human embryonic stem cell and a GSK-3 inhibitor.

A further aspect of the present invention relates to a method for treating a liver disease or for the reconstruction of a damaged liver in a subject, the method comprising administering to a subject a composition comprising a definitive endoderm cell and a GSK-3 inhibitor.

A further aspect of the present invention relates to a method for treating a liver disease or for the reconstruction of a damaged liver in a subject, the method comprising administering to a subject a composition comprising a cell or population of cells as described herein.

Preferably, the liver disease is associated with the loss of, damage to, or a lack of liver tissue. Examples of liver diseases include hepatitis, cirrhosis, haemochromatosis, Wilson's disease, phenylketonuria or genetic diseases affecting the liver (e.g. Crigler-Najjar syndrome).

A damaged liver may result, for example, following prolonged suffering from a liver disease or following surgery where part or all of the liver is removed. As such, the term "reconstruction of a damaged liver" may refer to reconstruction of all or part of a liver in a subject.

Preferably, the subject is a patient suffering from a liver disease or a patient who has undergone surgery to remove all or part of their liver. Preferably, the subject is a human.

The procedures required to administer a medicament according to the present invention will depend upon the nature of the liver disease or liver construction involved. Such procedures will be known to a person skilled in the art and can be applied accordingly. For example, it may be that a medicament or composition of the present invention can be administered via injection directly to the required site. Alternatively, the medicament or composition may be administered during surgery, for example following removal of a section of liver from a patient.

According to a further aspect of the present invention, there is provided use of a cell or population of cells described herein for screening for drug toxicity. For example, the hepatocyte-like cells described herein can be used in screening methods for drug toxicity.

In one aspect of the present invention, there is provided a method for assessing the toxicity of a compound to liver cells, the method comprising:

(i) incubating said compound with a cell or population of cells as described herein; and (ii) assessing the toxicity of the compound to the cell or population of cells, wherein said toxicity is indicative of liver toxicity.

Toxicity can be measured by methods known to those skilled in the art. In one example, cell death is indicative of toxicity of the compound toward a cell. In one example, the measurement of lactate dehydrogenase (LDH) released from lysed cells is indicative of toxicity. In another example, a change in the morphology of the cells is indicative of toxicity.

In one example, a decrease in the number of viable cells in a sample is indicative of toxicity of a compound. The number of viable cells in a sample may be counted after staining with a vital dye. Cell toxicity assay kits are commercially available and an example of such a kit is the TOX1 Cell toxicity Colorimetric Assay Kit from Sigma Aldrich which measures the activity of living cells via mitochondrial dehydrogenases.

Preferably, the cell or population of cells is a hepatocyte-like cell or population of hepatocyte-like cells, as described herein.

As such, in one embodiment, there is provided use of a hepatocyte-like cell or population of hepatocyte-like cells, as described herein, for assessing the toxicity of a compound to liver cells.

Preferably, the method is an in vitro method. Preferably, the method is indicative of in vivo liver toxicity of the compound.

Preferably, the GSK-3 inhibitor is a compound having the following structure, or a functional derivative, analogue or homologue thereof:

(A)

wherein, $R^1$ is H, a $C_1$-$C_6$ alkyl (preferably $CH_3$), or $CH_2O(CH_2)_2SiCH_3$;

$R^2$ is H, a $C_1$-$C_6$ alkyl (preferably $CH_3$), or $CH_2O(CH_2)_2SiCH_3$; or $R^1$ and $R^2$ together are —$(CH_2)_n$— unsubstituted or substituted by $OR^6$ or $R^7$, or —$(CH_2CH_2O)_m(CH_2)_2$—;

$R^3$ is H or a $C_1$-$C_6$ alkyl (preferably $CH_3$);

$R^4$ is H or a $C_1$-$C_6$ alkyl (preferably $CH_3$);

$R^5$ is H or $CH_2$aryl, wherein aryl is unsubstituted or substituted by alkoxy (preferably methoxy);

R⁶ is H, CH₂CH=CH₂, CH₂CH₂CH=CH₂, CH₂OCH₂CH=CH₂ or Si$^t$BuPh₂;

R⁷ is H, CH₂CH=CH₂, CH₂CH₂CH=CH₂, CH₂OCH₂CH=CH₂ or Si$^t$BuPh₂;

n is 6, 7, 8, 9, 10, or 11;

m is 3 or 4;

X and Y are each independently C or N.

Si$^t$BuPh₂ means tert-Butyldiphenylsilyl.

Preferably, R¹ and R² together are —(CH₂)$_p$CH(OR⁶)(CH₂)$_q$— or —CH(R⁷)(CH₂)$_q$—, wherein p is 1, 2, 3 or 4, and q is 4, 5, 6, 7, or 8.

The structures of preferred GSK-3 inhibitors are clearly derivable from Table 3 with reference to formula A above.

In particularly preferred embodiments, the GSK-3 inhibitor is selected from a compound having one of the following structures, or a functional derivative, analogue or homologue thereof:

(1O)

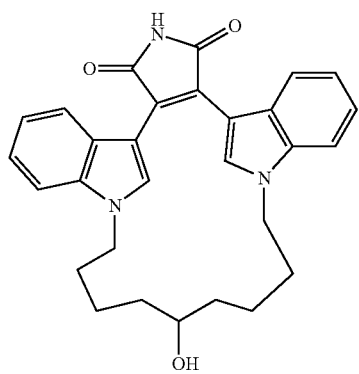

(1I)

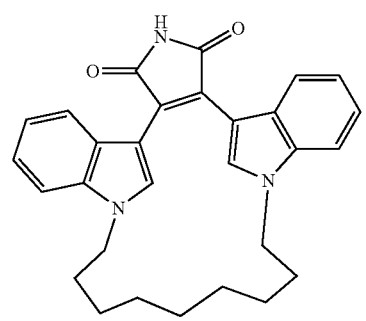

(1L)

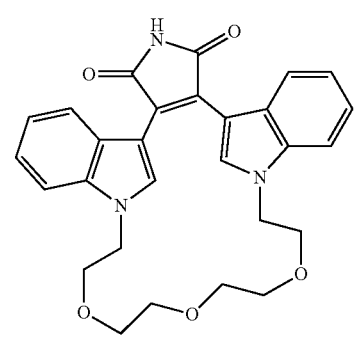

-continued (1M)

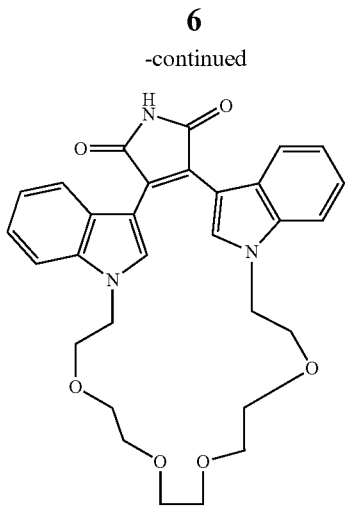

(2C)

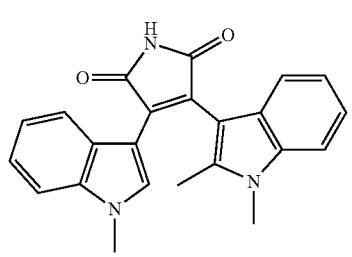

(2L)

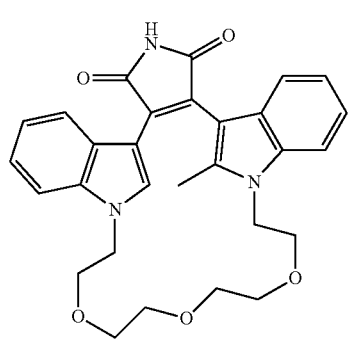

(4M)

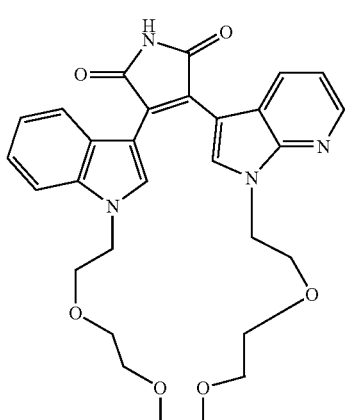

In other embodiments, the GSK-3 inhibitor is selected from a compound having one of the following structures, or a functional derivative, analogue or homologue thereof:

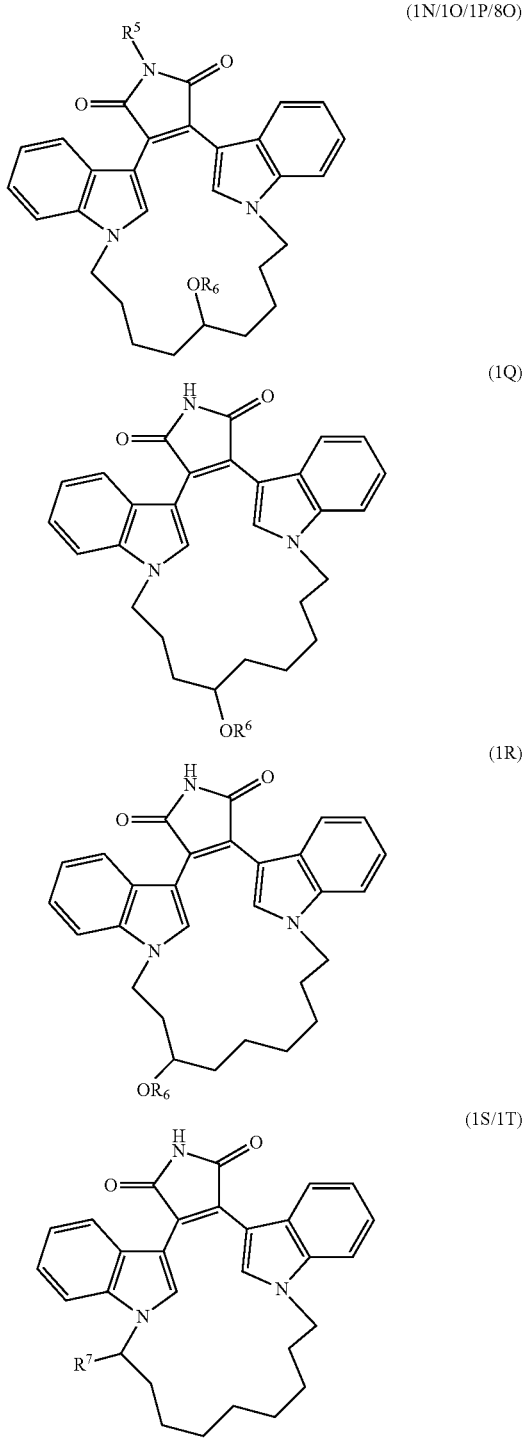

(1N/1O/1P/8O)

(1Q)

(1R)

(1S/1T)

wherein
R⁵ is H or CH₂Ph
R⁶ is H, CH₂CH=CH₂, CH₂CH₂CH=CH₂, CH₂OCH₂CH=CH₂ or Si'BuPh₂; and
R⁷ is H, CH₂CH=CH₂, CH₂CH₂CH=CH₂, CH₂OCH₂CH=CH₂ or Si'BuPh₂.

In other embodiments, the GSK-3 inhibitor is BIO, or a functional derivative, analogue or homologue thereof. BIO is a commercially available GSK-3 inhibitor with the following structure:

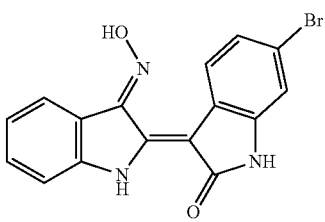 [SMILES: O=C1Nc2cc(Br)ccc2/C1=C1/Nc2ccccc2/C1=N\O]

In other embodiments, the GSK-3 inhibitor is CHIR99021, or a functional derivative, analogue or homologue thereof. CHIR99021 is a commercially available GSK-3 inhibitor with the following structure:

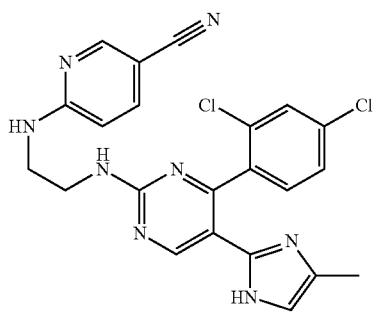 [SMILES: Cc1c[nH]c(-c2cnc(NCCNc3ccc(C#N)cn3)nc2-c2ccc(Cl)cc2Cl)n1]

Further GSK-3 inhibitors will be known to a person skilled in the art. In addition, a person skilled in the art will be able to ascertain whether a compound can function as a GSK-3 inhibitor by routine methods, such as those described in Bone et al (2009).

It will be appreciated that the human embryonic stem cells described herein can be obtained from a stem cell bank. As such, it will be appreciated that in order to repeat the invention defined herein, the destruction of a human embryo is not required. In addition to obtaining human embryonic stem cells from a stem cell bank (e.g. the UKSCB), it will be appreciated that other, non-embryo, sources exist. For example, as described by many groups, adult cells can be reprogrammed to pluripotent cells equivalent to embryonic stem cells. One example of this is as described by Takahashi et al (2007). Thus, where embryonic stem cells are referred to herein, this is intended to cover reprogrammed cells equivalent to embryonic stem cells, i.e. induced pluripotent stem cells.

Example embodiments of the present invention will now be described with reference to the accompanying figures.

DETAILED DESCRIPTION OF THE INVENTION

Figure 1:
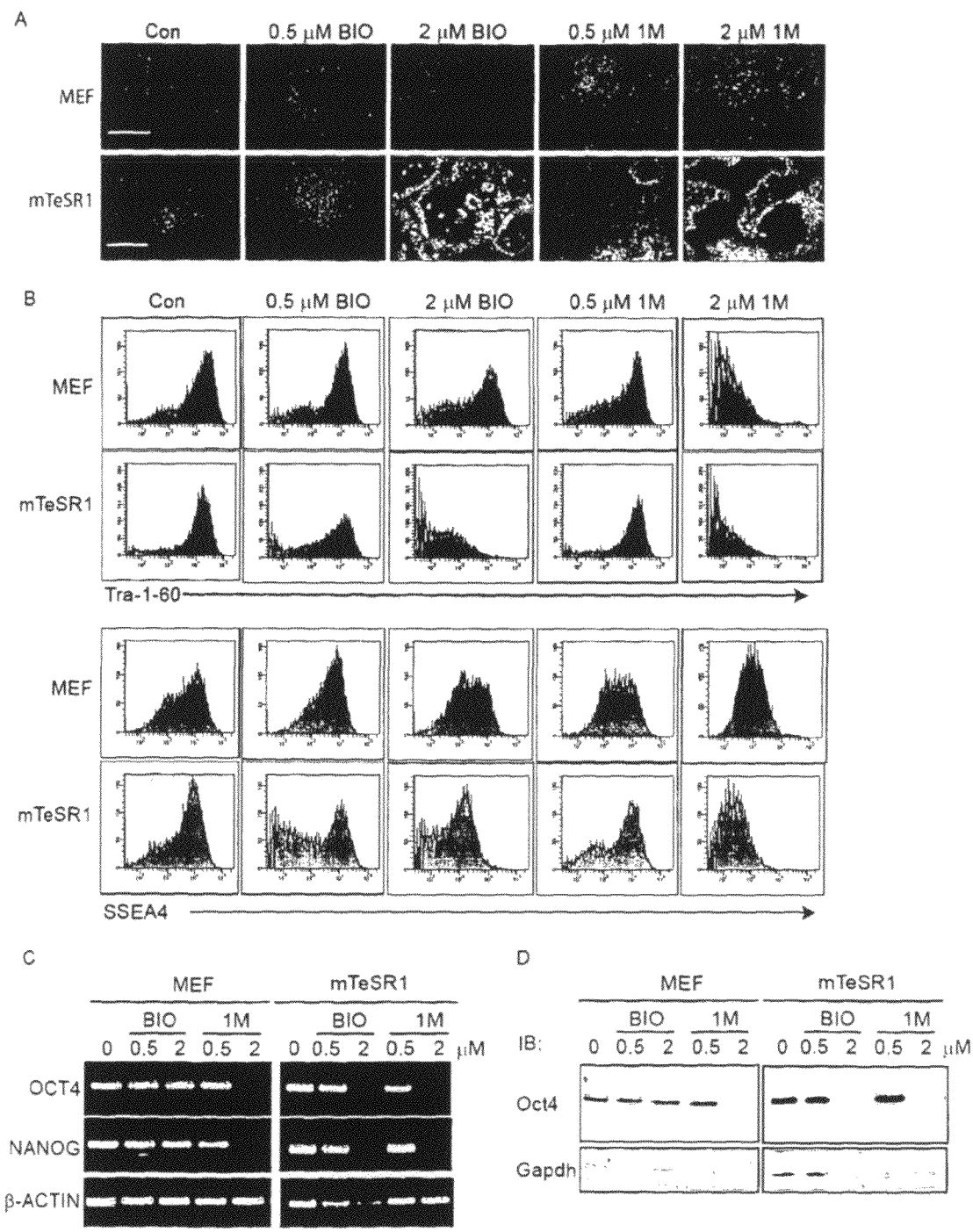
FIG. 1 shows that treatment of hESCs with 1M induces differentiation. Human ESCs [SHEF3] were treated with the indicated concentrations of BIO or compound 1M or left untreated as a control and cultured for 7 days. (A) Images show typical colonies formed following the indicated treatments. The scale bars represent 1 mm. (B) Histogram plots of ESCs analysed by flow cytometry following immunostaining with antibodies against the pluripotency markers Tra-1-60 or SSEA4. Analyses of percent positive cells and mean fluorescence intensity are given in Table 1. (C) RNA was extracted from the cells and RT-PCR analyses performed using primers specific to the pluripotency genes OCT4 and NANOG and to the house-keeping gene β-ACTIN. (D) Western blot analysis was performed on protein extracted from the cells and immunoblotted with antibodies specific to Oct4. Blots were stripped and reprobed with anti-Gapdh antibodies to assess equal loading. (E) Compound 1O also induces differentiation of human ESCs. SHEF3 cells were treated with the indicated concentration of 1O for 7 days. Images show typical colony morphology. (F) Histogram plots of ESCs analysed by flow cytometry following staining with Tra-1-60 and SSEA4 antibodies. Analysis of percent positive cells and mean fluorescent intensity are indicated on the plots. (G) RT PCR analysis for the expression of OCT4 and NANOG. Bands for each of the genes were from the same gel with intervening samples removed. (H) Western blot analysis of OCT4 protein expression. Proteins bands were from the same immunoblot with intervening samples removed.
Figure 1:
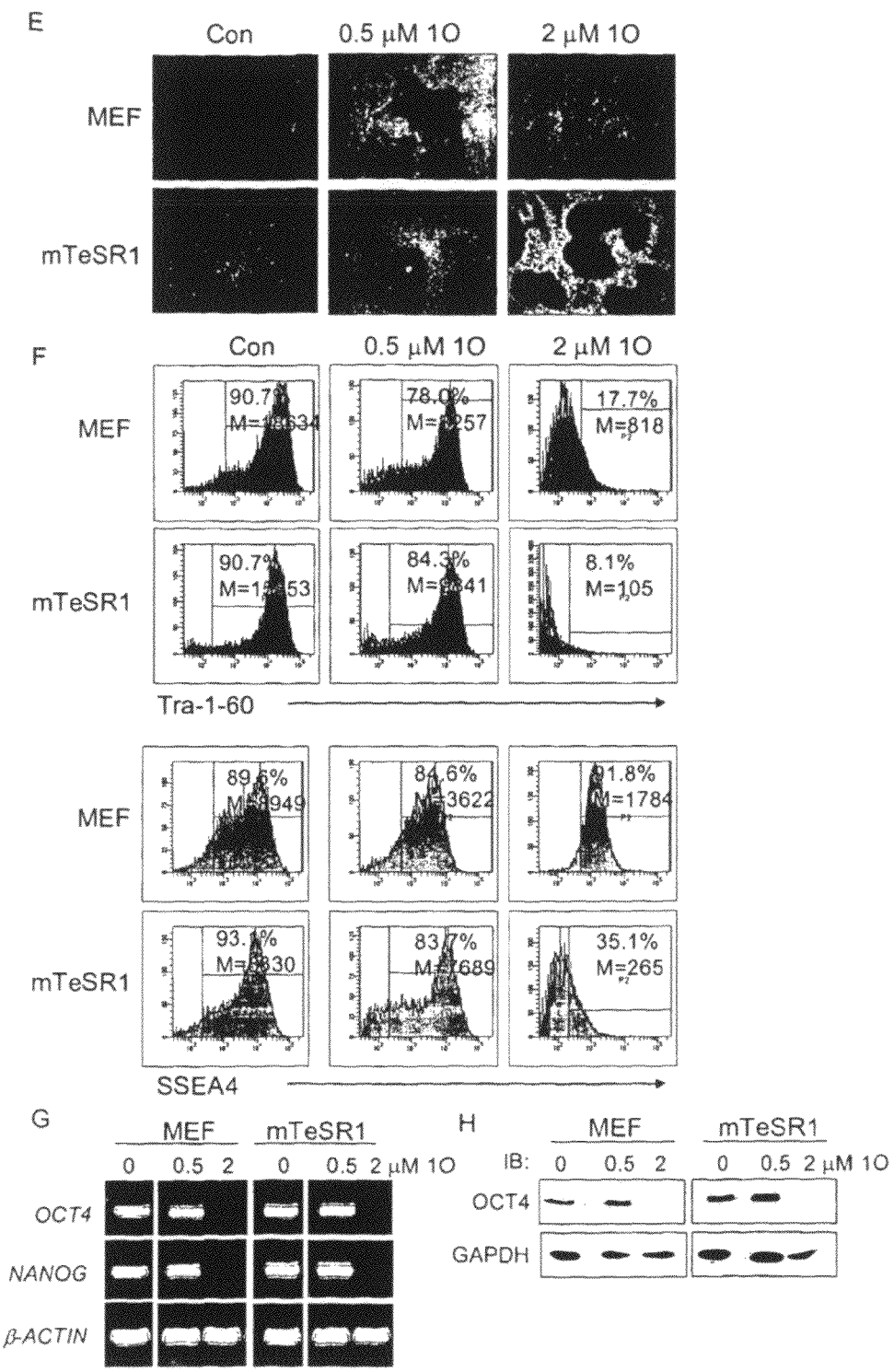

The invention relates to the use of GSK-3 inhibitors to direct differentiation of human embryonic stem cells towards cells of the definitive endoderm and to cells with a hepatocyte phenotype.

The use of small molecule inhibitors represents a powerful approach for efficiently and reproducibility directing differentiation of ESCs towards a desired cell type. A panel of compounds that inhibit GSK-3 in mouse ESCs has been previously synthesized and characterised, resulting in enhanced self-renewal (Bone et al., 2009). As described herein, treatment of human ESCs with one of these GSK-3 inhibitors, 1M, surprisingly results in differentiation towards the DE, with prolonged treatment resulting in generation of a population of cells displaying early hepatic characteristics. Intriguingly, 1M was capable of activating the Nodal signalling pathway and was better than Activin A for promoting differentiation. Importantly, 1M-derived endoderm was capable of generating cells with a more mature hepatocyte phenotype under defined culture conditions. Similar results were obtained with the structurally unrelated GSK-3 inhibitor BIO which was also capable of inducing differentiation of human ESCs towards the DE.

Furthermore, compounds in the same series as 1M, for example 1O and 1L were shown to have a similar capacity to induce hESC differentiation with compound 1L directing differentiation towards the DE.

The results described herein demonstrate that the methods of the present invention have a number of advantages over known protocols; they are simple and robust, requiring a single chemical entity to direct differentiation as far as the hepatoblast, they rely on monolayer based procedures, utilize chemically defined media, are applicable to distinct hESC lines and are readily scalable.

The methods used in the invention and detailed examples of the invention are set out below.

Within this specification embodiments have been described in a way which enables a clear and concise specification to be written, but it is intended and will be appreciated that embodiments may be variously combined or separated without parting from the invention.

Within this specification, the terms "comprises" and "comprising" are interpreted to mean "includes, among other things". These terms are not intended to be construed as "consists of only".

Reference to GSK-3 inhibition refers to inhibition of one or more GSK-3 enzymes. Thus a GSK-3 inhibitor can inhibit one member, several members or all members of the family of GSK-3 enzymes. The family of GSK-3 enzymes is well-known and includes but is not limited to GSK-3α and GSK-3β. A person skilled in the art will be able to ascertain whether a compound can function as a GSK-3 inhibitor by routine methods, such as those described in Bone et al (2009) and as described above in relation to FIG. 2.

The term "definitive endoderm" refers to one of the germ layers formed during animal embryogenesis. The definitive endoderm arises during the gastrulation stage of early embryogenesis when formation of the primary germ layers, the mesoderm, endoderm and ectoderm, occurs.

Within this specification, cells may be defined as being characteristic of "definitive endoderm" or being "definitive endoderm cells" if they are positive for the markers FoxA2, Sox17 and CXCR4.

Within this specification, cells may be defined as being "hepatocyte-like cells" if they are positive for the markers HNF4α, AFP, albumin and transthyretin.

Within this specification, the term "about" means plus or minus 20%, more preferably plus or minus 10%, even more preferably plus or minus 5%, most preferably plus or minus 2%.

The present invention is further intended to encompass, in addition to the use of the above listed compounds, the use of functional homologues, derivatives and analogues of such compounds. In this context, homologues are molecules having substantial structural similarities to the above-described compounds and analogues are molecules having substantial biological similarities regardless of structural similarities. The term 'derivatives' refers to molecules derived from the above-described compounds. Such derivatives may, for example, be chemical digestion products of the above-described compounds or synthetically altered derivatives of the above described compounds. The homologues, derivatives and analogues are said to be functional homologues, derivatives and analogues if they are able to inhibit GSK-3.

Results

Treatment with GSK-3 Inhibitor 1M Induces Differentiation of Human ESCs

A panel of compounds that inhibit GSK-3 in mouse ESCs is described in Bone et al., 2009. The compounds are more selective than commercially available inhibitors such as BIO and resulted in enhanced self-renewal.

It has now been found that, in contrast to the results observed in mice, treatment with the GSK-3 inhibitor, 1M, did not maintain self-renewal of human ESCs but instead induced differentiation. This was truly surprising and unexpected.

Treatment of human ESCs with 2 μM compound 1M over a 7 day time period led to a dramatic increase in proliferation and differentiation when cultured on either MEFs in KO DMEM or in a feeder-free, chemically defined system on Matrigel® in mTeSR1® media (FIG. 1). This was reflected in analyses of surface markers by flow cytometry which showed a dramatic decrease in expression of the pluripotency markers Tra-1-60 and SSEA4 following treatment with 1M (FIG. 1B; Table 1). Gene expression analyses also showed loss of the pluripotency markers OCT4 and NANOG (FIG. 1C) and there is also loss of Oct4 protein expression (FIG. 1D). These results were observed in both SHEF1 and SHEF3 cell lines and indicate that the GSK-3 inhibitor 1M has a robust and dramatic effect on human ESCs resulting in loss of pluripotency and an increase in proliferation. In addition, treatment of SHEF3 ESCs with compound 10 also induced similar differentiation under both culture conditions (FIG. 1E). Again, this was demonstrated by decreased expression of Tra-1-60 and SSEA4 by flow cytometry (FIG. 1F), loss of OCT4 and NANOG gene expression (FIG. 1G) and loss of OCT4 protein expression (FIG. 1H).

Figure 2:
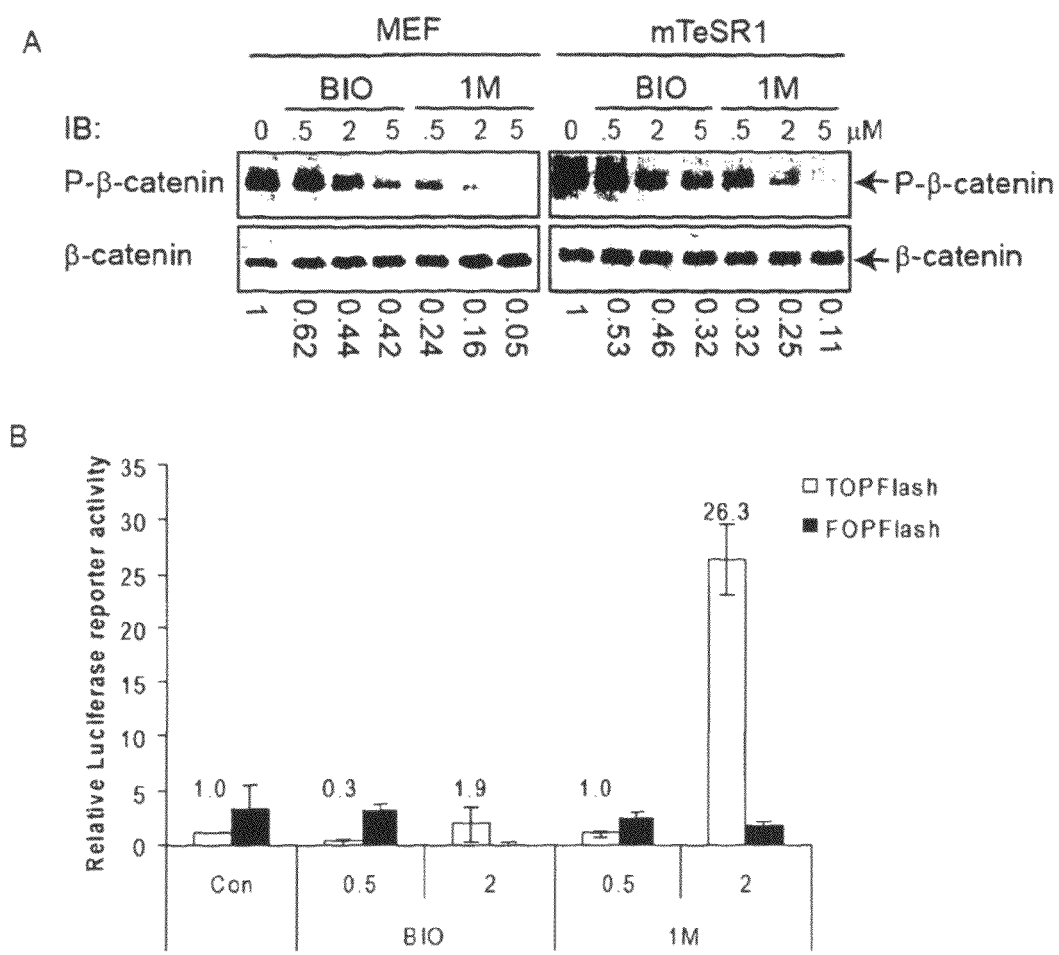
FIG. 2 shows that treatment of hESCs with compound 1M inhibits GSK-3-mediated signaling. (A) ESCs [SHEF3] were cultured on MEFs or on Matrigel® in mTeSR1® media and treated with BIO or 1M for 30 min. Protein extracts were prepared and immunoblotting was performed using antibodies detecting the phosphorylated form of β-catenin. The same immunoblot in each case was reprobed for total β-catenin to assess loading. (B) TOPFlash luciferase reporter assay of ESCs [SHEF1] treated for 24 hr with BIO or 1M at the indicated concentrations. Luciferase activity is expressed as a fold increase in activation compared with the normalised TOPFlash luciferase activity in untreated (Con) cells. Data represent the mean+/−SEM of 3 independent experiments. Similar results were observed in SHEF3 ESCs.

Since compound 1M was robustly promoting differentiation in human ESCs, as opposed to the self-renewal previously observed in mouse ESCs, its ability to inhibit GSK-3 in human ESCs has also now been confirmed. The results are shown in FIG. 2.

1M Treatment of Human ESCs Induces Differentiation Towards the DE

Having observed that treatment of human ESCs with the small molecule GSK-3 inhibitor 1M promotes differentiation, it was next determined towards which lineage the cells were differentiating.

Figure 3:
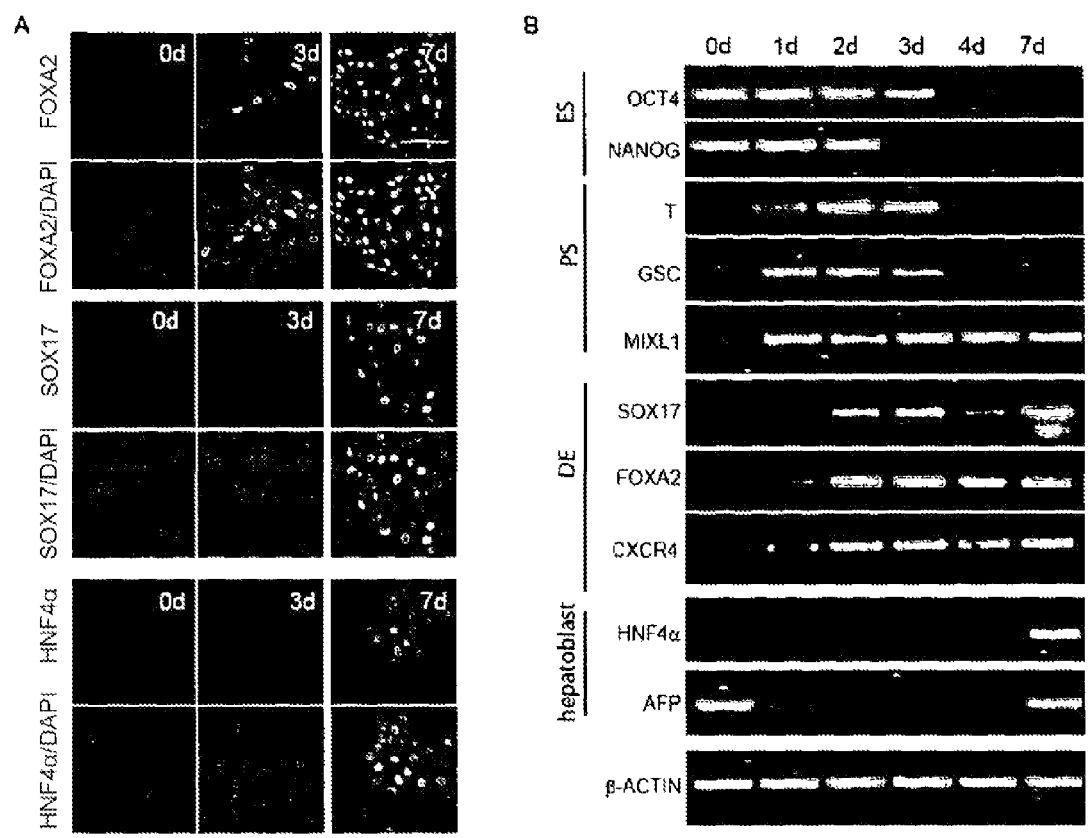
FIG. 3 shows that 1M treatment induces differentiation towards the definitive endoderm. Human ESCs [SHEF3] were maintained feeder-free on Matrigel® in chemically defined mTeSR1® media and treated with 2 μM 1M for the days indicated. (A) Expression of the endodermal markers FoxA2, Sox17 and HNF4α were analysed by immunofluorescence. Treatment with compound 1M led to expression of all markers after 7 days treatment. Scale bar represents 50 μm. (B) ESCs were harvested on day 7 following treatment with 1M for the indicated days. RNA was extracted and RT-PCR analyses performed using primers selective for the genes indicated. Similar results were observed in SHEF1 human ESCs. (C) BIO induces differentiation towards the DE. SHEF3 ESCs were treated with 2 μM BIO for the times indicated and immunostained with antibodies towards the endodermal markers FOXA2, SOX17 and HNF4α. (D) Compound 1L also induces differentiation towards the DE. SHEF1 ESCs were treated with 2 μM 1L for the times indicated and immunostained with antibodies towards the endodermal markers FOXA2 and HNF4α.
Figure 3:
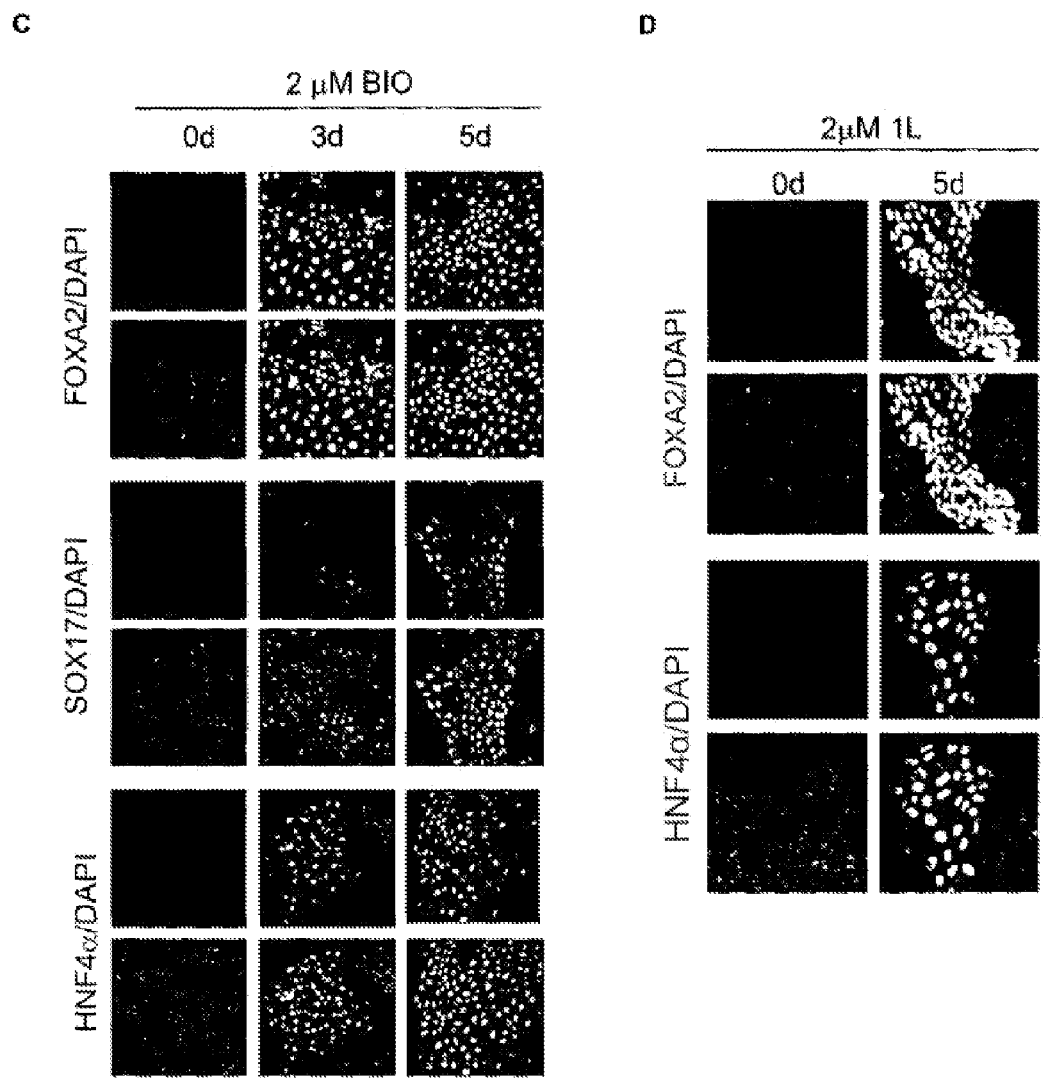

The following experiments were all performed on human ESCs cultured feeder-free on Matrigel® in chemically defined mTeSR1® media. This system has the advantages of simplicity and reliability, leading to consistency and reproducibility of cell culture and differentiation. Immunostaining of 1M-treated human ESCs with antibodies towards transcription factors expressed in the DE, FoxA2, Sox17 and hepatocyte nuclear factor 4α (HNF4α) indicated that the cells were differentiating towards the DE in a time dependent manner (FIG. 3A). Gene expression analyses over the 7 days of differentiation showed the progression of differentiation though the PS towards the DE (FIG. 3B). Induction of differentiation was indicated by loss of OCT4 and NANOG expression. Initially upregulation of Brachyury (T) which defines the formation of the PS and is downregulated in DE was observed. Other primitive streak markers goosecoid (GSC) and MIXL1 were likewise upregulated at an early time point. This was followed by expression of hepatocyte nuclear factor (HNF) 3β (FOXA2) and CXCR4, which are expressed in the PS and are maintained in DE progenitors, and the DE marker SOX17. SOX17 and FOXA2 are expressed not only in the DE but also in the primitive endoderm. However, CXCR4 is expressed in the DE and mesoderm but not in the primitive endoderm (McGrath et al., 1999) and has been used as a marker to distinguish between primitive endoderm and definitive endoderm in mouse (Yasunaga et al., 2005) and human (D'Amour et al., 2005) ESCs. Importantly, ESCs (enriched for the surface receptors CXCR4), differentiate into endoderm cells with either hepatocytic phenotype (Gouon-Evans et al., 2006) or pancreatic endocrine cells (D'Amour et al., 2006). Expression of SOX17, GSC and FOXA2 are not a result of differentiation to primitive endoderm. Interestingly, following 7 days treatment with 1M, expression of HNF4α and α-fetoprotein (AFP) was observed. Although AFP is a marker for primitive (visceral) endoderm at the early stages of development, later it marks the earliest specification to the hepatic lineage. HNF4α is a key transcription factor that regulates a cascade of liver-specific transcription. Together, the expression of AFP and HNF4α by day 7, suggests maturation of the DE-specified cells towards an early hepatic lineage.

Treatment with BIO also induced differentiation towards the DE (FIG. 3C) as indicated by immunostaining with antibodies towards the DE markers FOXA2, SOX17 and HNF4α. Similarly, treatment of SHEF3 ESCs with compound 1L also induced differentiation towards the DE (FIG. 3D).

Involvement of Activin/Nodal Signalling in 1M-induced DE

Figure 4:
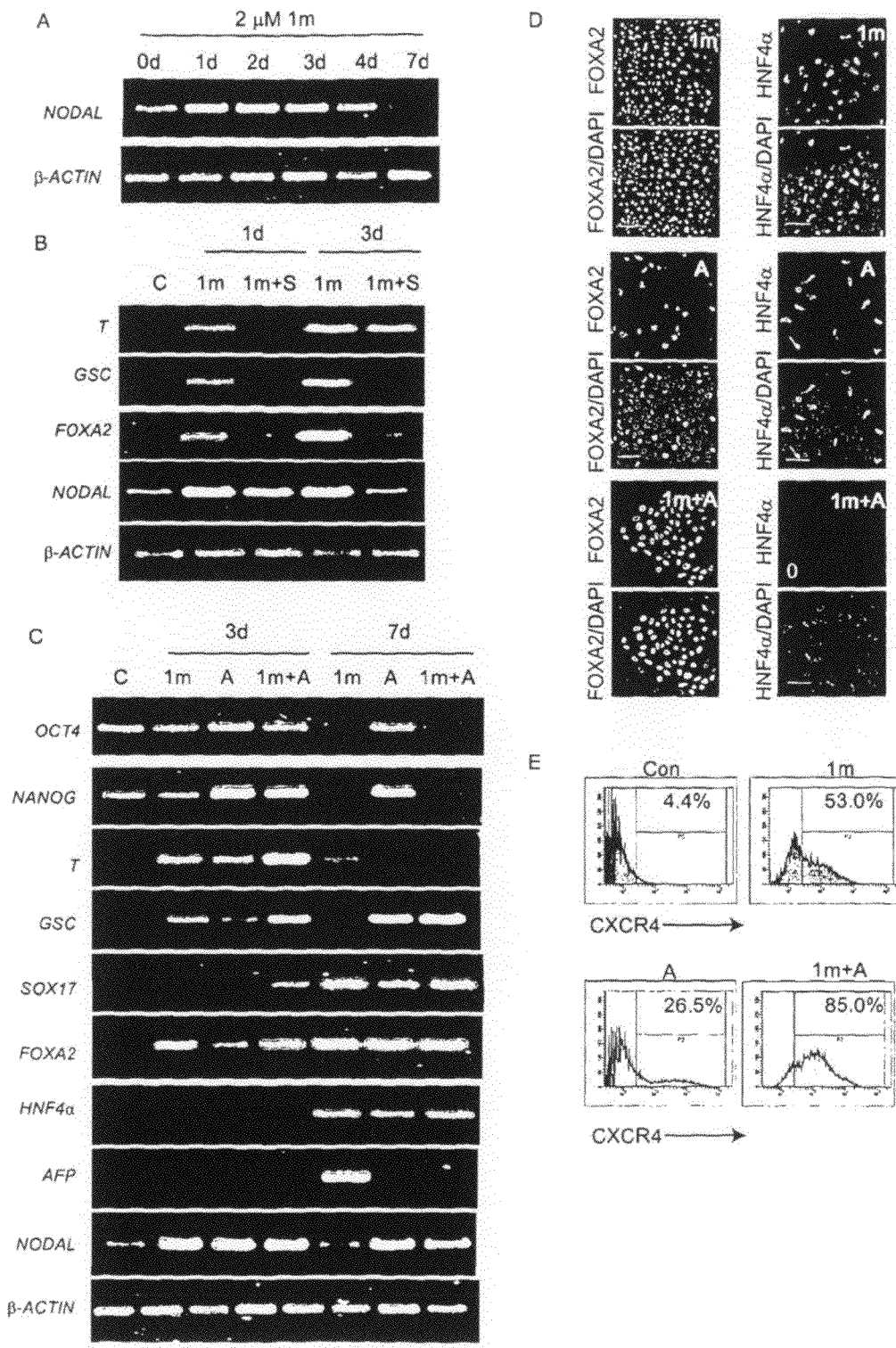
FIG. 4 shows that 1M induces activation of the Activin/Nodal pathway. (A) RNA was extracted from ESCs [SHEF1] cultured for 7 days in the presence of 2 μM 1M for the days indicated. RT-PCR analyses were performed using primers selective for the genes indicated. (B) ESCs [SHEF1] were treated with 2 μM 1M alone or in combination with 10 μM SB43125 (S) for the days indicated and RT-PCR performed on the extracted RNA. (C) ESCs [SHEF3] were treated with 1M alone or in combination with 100 ng/ml Activin A (A) for the days indicated and RT-PCR performed. (D). ESCs [SHEF1] were treated with 2 μM 1M, or 100 ng/ml ActivinA (A) alone or in combination with 1M for 5 days. Expression of the endoderm markers FoxA2 and HNF4α was analysed by immunofluorescence. The number of percent positive cells averaged from 3 fields of view +/−SD are indicated. Scale bar represents 50 μm. (E) ESCs [SHEF1] were treated with 2 μM 1M, or 100 ng/ml ActivinA (A) alone or in combination with 1M for 5 days. Expression of the DE marker CXCR4 was alaysed by flow cytometry.

During early embryogenesis, the TGFβ signalling pathway is involved in the formation of the PS, mesoderm and DE. High levels of Nodal, a member of the TFGβ superfamily, are required for the specification of the endoderm following transition of precursor cells through the anterior region of the PS. Activin is another member of the TGFβ superfamily which binds to the same receptors as Nodal and is used to mimic Nodal activity in vitro. In human ESCs, generation of DE has relied on activation of the Activin/Nodal pathway (D'Amour et al., 2005). Therefore, it was next determined whether the 1M compound was also activating the Nodal pathway. Indeed, following treatment for only 1 day with 1M, an increase in NODAL gene expression was seen which was maintained for up to 3 days and then declined to basal levels by day 7 (despite the media being changed with fresh compound every-other day) (FIG. 4A). Induction of NODAL expression was only partially inhibited by the Activin receptor-like kinase 4/5/7 (ALK) inhibitor SB43125 (FIG. 4B). However, treatment with SB34125 dramatically reduced 1M-induced GSC and FOXA2 expression, downstream targets of Nodal signalling. These data indicate that 1M is either directly or indirectly activating the Nodal signalling pathway which is required for 1M-induced DE formation.

Next the efficiency of 1M-induced DE formation compared with Activin A treatment alone or in combination with 1M was explored. Gene expression analyses (FIG. 4C) indicated that following 3 days treatment, 1M induced similar levels of expression of the PS markers T and GSC compared with ActivinA alone; although there appeared to be slightly higher expression in combination with Activin A. Following 7 days induction, little or no T or GSC expression was observed following 1M treatment alone, indicating transition through the PS. GSC expression was maintained in the presence of Activin A (alone or in combination with 1M) as GSC is a downstream transcriptional target of Nodal signalling. Expression of DE markers SOX17 and FOXA2 and the early liver-specific transcription factor HNF4α appeared similar following treatment with 1M either alone or in combination with Activin A.

Intriguingly, 1M-induced expression of AFP was lost in the presence of Activin A. Nodal signalling persists during gastrulation until formation of the DE, after which expression falls allowing maturation and gut tube formation (Collingnon et al, 1996). Recently in mouse ESCs, induced Nodal expression resulted in DE specification and subsequent downregulation of Nodal promoted maturation of the DE (Takenaga et al., 2007). Here, 1M-induced AFP expression also correlated with decreased Nodal gene expression. Inhibition of DE maturation by sustained Activin/Nodal signalling may be a result of maintained OCT4 expression. Nodal signalling is involved in the maintenance of pluripotency and is essential in maintaining OCT4 expression during gastrulation. Both the pluripotency markers NANOG and OCT4 are maintained following treatment with Activin A for 7 days. However, in the presence of 1M, Activin A-induced expression of OCT4 and NANOG are not maintained, although elevated levels of GSC suggest inhibition of 1M-induced maturation from the PS stage in the presence of Activin A. These results suggest that 1M-induced transient activation of the Nodal signalling pathway results in specification to the DE and its subsequent maturation to an early hepatic phenotype.

To further examine the efficiency of DE formation FoxA2 and HNF4α expression was analysed by immunofluorescence (FIG. 4D). Treatment with 1M for 5 days lead to clusters of cells expressing a high proportion of FoxA2 (73% positive), whereas expression of FOXA2 in the entire population was 35-40%. Activin A treatment generated a lower proportion of cells expressing FOXA2 (on average 8%) which were dispersed throughout the population.

Addition of Activin A did not further enhance 1M-induced FoxA2 expression. Compound 1M also appeared to generate more HNF4α-expressing cells (20%) than Activin A alone (3%). Interestingly, Activin A appeared to inhibit generation of 1M-induced HNF4α expressing cells. Analyses of CXCR4 expression by flow cytometry (FIG. 4E) indicated that treatment with 1M led to enhanced CXCR4 expression (53.0%) as compared with Activin A alone (26.5%), whereas 1M in combination with Activin A further increased CXCR4 expression (85.0%).

The results obtained show that under the culture conditions described herein, the efficiency of 1M-induced DE formation is similar or better than Activin A alone. 1M treatment in combination with Activin A may lead to increased DE formation as assessed by CXCR4 expression but inhibits further differentiation towards an early hepatic phenotype with loss of HNF4α and AFP expression.

1M-induced DE has Hepatocyte-like Potential in vitro

Figure 5:
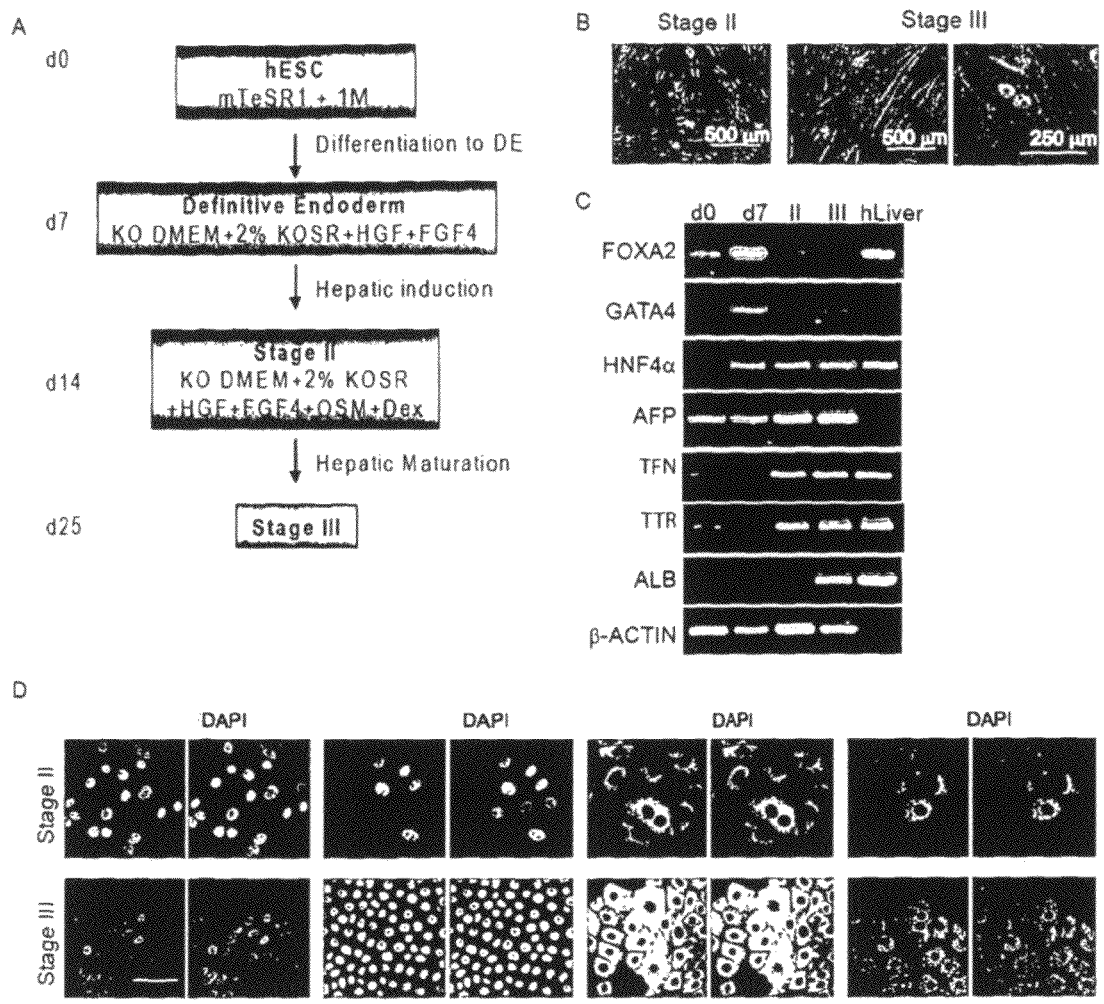
FIG. 5 shows differentiation of human ESCs to hepatocyte-like cells. (A) Schematic representation of the differentiation protocol. (B) Images of differentiated cells at stage II (d14) and stage III (d25). (C) RT-PCR expression analyses of RNA prepared from cells at the indicated stages of differentiation, using primers specific to the genes indicated. RNA extracted from human liver was used as a positive control. β-ACTIN was used as a housekeeping gene. (D) Expression of FoxA2 and the early hepatic markers HNF4α, AFP and TTR in cells at stage II and stage III of differentiation were analyzed by immunofluorescence. Scale bar represents 50 μm. (E) Media (1 μl) from stage III (d25) cells, conditioned for 48 hours, and from a media alone (MA) control were analysed by immunoblotting with an antibody to AFP. Purified AFP and media conditioned from HUH7 cells were run as controls. (F) ELISA assay for human Albumin from stage III (d25) media. (G) Differentiation of BIO-derived DE cells to hepatocyte-like cells. SHEF3 ESCs were treated with 2 μM BIO for 5 days to induce differentiation to the DE. ESCs were then cultured under hepatic induction and maturation conditions as outlined in the Experimental Procedures and FIG. 5A. Expression of FOXA2 and the early hepatic markers HNF4α, AFP and TTR in ESCs at stage II and stage III of differentiation were analyzed by immunofluorescence. Scale bar represents 50 μm. (H) RT-PCR expression analyses of RNA prepared from cells at the indicated stages of differentiation following BIO-induced DE differentiation, using primers specific to the genes indicated.
Figure 5:
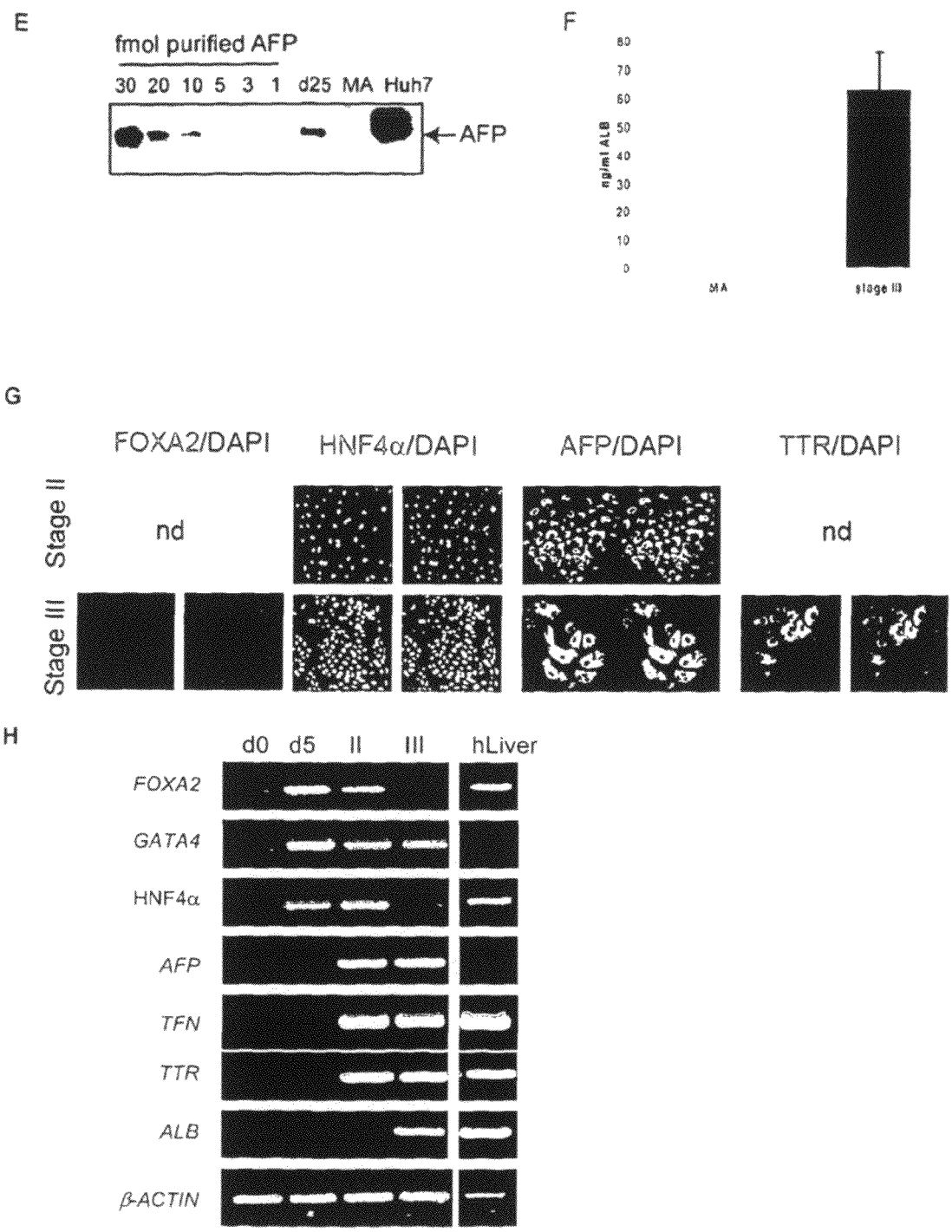

Next, the potential of chemically induced DE to generate hepatocyte-like cells (HLCs) was investigated. The ability to generate HLCs provides an indication of the developmental potential of the chemically derived DE with the ultimate aim of generating functional HLCs. To begin to address this potential, a differentiation protocol based on work by Argawal et al, 2008 (Agarwal et al., 2008) was employed, to generate HLCs as outlined in Experimental Procedures and FIG. 5A. Following 1M-induced generation of DE, hepatic induction was initiated by culturing in hepatocyte growth factor (HGF) and fibroblast growth factor 4 (FGF4), followed by a cocktail of HGF, FGF4, Oncostatin M (OSM) and dexmethasone (Dex) to induce maturation of the HLCs. Following hepatic induction (stage II), the cells begin to adopt hepatic characteristics (FIG. 5B). They expressed increased levels of AFP and expression of albumin (ALB), transferrin (TFN) and transthyrettin (TTR) was started to be seen, correlating with initial hepatic differentiation (FIG. 5C). Following the hepatic maturation step, stage III cells had characteristics of hepatocytes with polygonal morphology, distinct, round nuclei with 1 or 2 prominent nucleoli, and many were binucleate. Compared with stage II cells, the matured cells had increased ALB gene expression (FIG. 5C) and increased HNF4α, AFP and TTR protein, as detected by immunostaining (FIG. 5D). To assess liver-specific function, secretion of key serum proteins, AFP and Albumin were determined. Both AFP and Albumin (FIGS. 5E and 5F) were detected in the media of stage III cells derived from 1M induced DE. These results indicate that 1M-derived definitive endoderm has the potential to differentiate into cells with hepatocyte characteristics. Similar results were also generated using BIO-derived DE cells (FIGS. 5G and H).

Experimental Procedures

Cell Culture

SHEF1 and SHEF3 human ESCs were obtained from the UKSCB and cultured as outlined in their protocols. Briefly, ESCs were maintained on mitomycin C-inactivated mouse embryonic fibroblast (MEF) feeder layers in KnockOut Dulbecco's modified Eagle's medium (KO DMEM) (Invitrogen) supplemented with 20% (vol/vol) KO serum replacement (KOSR; Invitrogen), 1 mM non-essential amino acids (NEAA; Invitrogen), 1 mM glutamine (Invitrogen), 0.1 mM 2-mercaptoethanol (BioRad), penicillin/streptomycin, and 4 ng/ml recombinant human FGF2 (Peprotech). Cultures were passage using 1 mg/ml collagenase at a ratio of 1:8 to 1:12 every 7 days. Cultures were transferred to a feeder-free, chemically defined culture system on ESC-qualified Matrigel® (BD) coated plates in mTeSR1® (Stem Cell Technologies) media according to Stem Cell Technologies' protocol.

Differentiation to Definitive Endoderm and Hepatocyte-like cells

ESCs were cultured feeder-free on Matrigel®-coated plates in mTeSR1® media, supplemented with 2 μM compound 1M for 7 days with the media being refreshed every-other day. Definitive endoderm cultures were passaged with collagenase (1 mg/ml) and plated at a ratio of 1:10 on Matrigel® in KO DMEM supplemented with glutamine, penicillin/streptomycin, NEAA, 2% (v/v) KOSR, 10 ng/ml HGF (Peprotech) and 10 ng/ml FGF4 and cultured for a further 7 days with the media being refreshed every-other day. To allow for maturation of the HLCs, 10 ng/ml oncostatin M (Peprotech) and $10^{-7}$ dexamethasone (SIGMA) were added to the above media and the cells were cultured for an additional 7 days with fresh media every-other day.

Reverse Transcription-Polymerase Chain Reaction

Total RNA was isolated and purified using TRIzol Reagent (Invitrogen), following the manufacturer's instructions. All RNA samples were treated with DNase I (Ambion) before cDNA synthesis to eliminate any contaminating genomic DNA. RNA (1 μg) was reverse transcribed into cDNA using Oligo(dT)$_{15}$ (Promega) and SuperScript II (Invitrogen). Gene-specific PCR was carried out using primers and annealing temperatures outlined in Table 2.

Immunoblotting

Cell lysates (20 μg) were prepared, separated by SDS-PAGE and transferred to nitrocellulose as described previously (Welham et al., 1994). Immunoblotting was carried out using primary antibodies at the following dilutions: 1:5,000 anti-Oct4 (Santa Cruz Biotechnology; sc-9081); 1:2000 anti-GAPDH (sc-20357); 1:10,000 anti-phospho (Ser33/37/Thr41) β-catenin (Cell signalling Technology; CST 9561); 1:1000 anti-β-catenin (CST 9562). Anti-rabbit antibodies conjugated to horseradish peroxidise (DAKO) were used at 1:10,000 and blots were developed using ECL Advance (GE Healthcare) or ChemiGlow (Alpha Innotech) according to manufacturer's directions. Images were captured and analysed using the ImageQuant RT ECL system (GE Healthcare). Blots were stripped and reprobed as described previously (Welham et al., 1994).

Flow Cytometry

ESCs were trypsinised (0.05% Trypsin-EDTA) for 10 minutes at 37° C. and resuspended in PBS containing 2% (v/v) FBS (FBS/PBS). Cells were then stained on ice for 45 minutes with antibodies towards Tra-1-60 (10 μg/ml; Abcam), SSEA4 (15 μg/ml; clone MC813 Abcam), or phycoerythrin (PE)-conjugated anti-CXCR4 (1:100; clone12G5; R&D Systems). Cells were washed and stained with secondary fluorescein isothiocyanate (FITC)-conjugated antibodies (SIGMA) for a further 30 minutes, if required. Flow cytometry was performed using a FACSCanto cytometer (Becton Dickenson) and the data were analysed with FACSDiva software. Dead cells were excluded for analyses based on forward and side scatter parameters.

Luciferase Reporter Assay to Measure β-catenin-mediated Transcriptional Activity The TOPFlash luciferase reporter plasmid (containing four consensus TCF binding sites upstream of the c-fos minimal promoter, driving expression of a firefly luciferase reporter) and its negative control plasmid FOPFlash (containing four mutant TCF binding sites) were provided by Dr C. Dani (CNRS, Nice, France). To normalise the assay, the Renilla luciferase control vector phRL-TK (Promega) was included as an internal control. ESCs were plated on Matrigel®-coated 24-well plates for 5 days and then transfected with 0.6 g TOPFlash (or FOPFlash) and 0.144 μg phRL-TK mixed with 3 μl lipofectamine 2000 (Invitrogen). The transfection mixture (0.1 ml) was added to the cells in 0.5 ml fresh mTeSR1 ®. Following 24 hours, the media was replaced, containing the indicated compounds, and allowed to incubate a further 24 hours. Cell extracts were prepared and firefly and Renilla luciferase activities were determined using the dual-luciferase reporter assay system according to the manufacturer's instructions (Promega). TOPFlash (FOPFlash) firefly luciferase activities were normalised to those of co-transfected phRL-TK Renilla luciferase activity. Data are represented as fold increase above unstimulated control FOPFlash values.

Immunofluorescence

ESCs were cultured on Matrigel®-coated lummox (Greiner Bio One) trays and fixed with 4% paraformaldehyde (PFA) for 20 minutes at room temperature. Cells were permeabilised in PBST (with 0.1% Triton X-100) and blocked in 10% blocking reagent (Roche) before incubating with primary antibodies in 2% blocking reagent overnight at 4° C. After washing in PBS, cells were incubated with FITC-conjugated secondary antibodies (Vector Labs) for 3 hours at room temperature. After further washing, the cells were stained with 4,6-diamidino-2-phenylindole (DAPI) (SIGMA), washed again and mounted in MOWIOL. The following antibodies and dilutions were used: goat-anti-FoxA2 (1:100, R&D. Systems), mouse anti-Sox17 (1:50, R&D Systems), rabbit anti-HNF4α (1:100, Santa Cruz), rabbit anti-AFP (1:100, DAKO), rabbit anti-TTR (1:100, DAKO). Images were captured on a Zeiss 510 Meta confocal microscope using a 40× objective.

TABLE 1

Flow cytometry analyses of human ESCs treated with BIO and compound 1M

| | | | Con | 0.5 BIO | 2 BIO | 0.5 1M | 2 1M |
|---|---|---|---|---|---|---|---|
| MEF | Tra1-60 | % pos | 90.7 | 82.2 | 75.1 | 82.1 | 18.9 |
| | | mean | 18634 | 9497 | 7441 | 9403 | 1092 |
| | SSEA4 | % pos | 89.6 | 91.3 | 83.3 | 90.4 | 72.9 |
| | | mean | 8949 | 6002 | 4006 | 5805 | 1656 |
| mTeSR1 | Tra1-60 | % pos | 90.7 | 73.7 | 40.5 | 85.9 | 25.6 |
| | | mean | 15853 | 8194 | 890 | 11955 | 312 |
| | SSEA4 | % pos | 93.1 | 69.2 | 72.5 | 88.6 | 52.9 |
| | | mean | 8330 | 5871 | 1410 | 7578 | 465 |

TABLE 2

PCR Primers

| Name | Forward Primer (5'-3') | Reverse Primer (5'-3') | Ta (°C.) |
|---|---|---|---|
| AFP | GAGATGTGCTGGATTGTCTGC (SEQ ID NO: 1) | TAACTCCTGGTATCCTTTAGC (SEQ ID NO: 2) | 60 |
| ALB | CCTTTGGCACAATGAAGTGGGTAACC (SEQ ID NO: 3) | CAGCAGTCAGCCATTTCACCATAGG (SEQ ID NO: 4) | 55 |
| BRACH | GCCCTCTCCCTCCCCTCCACGC (SEQ ID NO: 5) | CCGTTGCTCACAGACCACAGG (SEQ ID NO: 6) | 62 |
| CER1 | GACAGTGCCCTTCAGCCAG (SEQ ID NO: 7) | GTTCAGTGCAGTTCAGTGG (SEQ ID NO: 8) | 56 |
| CXCR4 | CCGCATCTGGAGAACCAGC (SEQ ID NO: 9) | GGTGCAGCCTGTACTTGTCCG (SEQ ID NO: 10) | 60 |
| FOXA2 | AGATGGAAGGGCACGAGC (SEQ ID NO: 11) | CAGGCCGGCGTTGATGTT (SEQ ID NO: 12) | 56 |
| GSC | AGCAGTGCTCCTGCGTCCCGA (SEQ ID NO: 13) | CTCTGATGAGGACCGCTTCTG (SEQ ID NO: 14) | 66 |
| HNF4α | TGGCGAGCACCTGCTGCTCGG (SEQ ID NO: 15) | ATCTGCCACGTGATGCTCTGC (SEQ ID NO: 16) | 60 |
| MIXL1 | TACCCCGACATCCACTTGC (SEQ ID NO: 17) | CAGGCAGTTCACATCTACC (SEQ ID NO: 18) | 54 |
| NANOG | CCTGATTCTTCCACCAGTCCC (SEQ ID NO: 19) | GTCGGGTTCACCAGGCATCCC (SEQ ID NO: 20) | 65 |
| NODAL | CCGAGGGCAGACATCATCC (SEQ ID NO: 21) | TAGGTCCATCTGAAACCGC (SEQ ID NO: 22) | 56 |
| OCT4 | TGAGGGTGAAGCAGGAGTCGG (SEQ ID NO: 23) | AAGATTTTCATTGTTGTCAGC (SEQ ID NO: 24) | 58 |
| SOX17 | TCATGGTGTGGGCTAAGGACG (SEQ ID NO: 25) | CGGTACTTGTAGTTGGGGTGG (SEQ ID NO: 26) | 58 |
| TFN | AGAAGGGAGATGTGGCCTTT (SEQ ID NO: 27) | CGACCGGAACAAACAAAACT (SEQ ID NO: 28) | 56 |
| TTR | CCACTCATTCTTGGCAGGCT (SEQ ID NO: 29) | AGGTGTCATCAGCAGCCTTT (SEQ ID NO: 30) | 58 |
| β-ACTIN | TAGGCACCAGGGTGTGATGG (SEQ ID NO: 31) | CATGGCTGGGGTGTTGAAGG (SEQ ID NO: 32) | 62 |

TABLE 3

Preferred GSK-3 inhibitors

| Name | X | Y | $R^1$ | $R^2$ | $R^3$ | $R^4$ | $R^5$ | $R^6/R^7$ |
|---|---|---|---|---|---|---|---|---|
| 1a | C | C | H | H | H | H | H | — |
| 1c | C | C | $CH_3$ | $CH_3$ | H | H | H | — |
| 1e | C | C | $CH_2O(CH_2)_2SiCH_3$ | $CH_2O(CH_2)_2SiCH_3$ | H | H | H | — |
| 1g | C | C | $R^1$ and $R^2$ together are —$(CH_2)_7$— | | H | H | H | — |
| 1h | C | C | $R^1$ and $R^2$ together are —$(CH_2)_8$— | | H | H | H | — |
| 1i | C | C | $R^1$ and $R^2$ together are —$(CH_2)_9$— | | H | H | H | — |
| 1k | C | C | $R^1$ and $R^2$ together are —$(CH_2)_{11}$— | | H | H | H | — |
| 1l | C | C | $R^1$ and $R^2$ together are —$(CH_2CH_2O)_3(CH_2)_2$— | | H | H | H | — |
| 1m | C | C | $R^1$ and $R^2$ together are —$(CH_2CH_2O)_4(CH_2)_2$— | | H | H | H | — |
| 2a | C | C | H | H | H | $CH_3$ | H | — |
| 2b | C | C | $CH_3$ | H | H | $CH_3$ | H | — |
| 2c | C | C | $CH_3$ | $CH_3$ | H | $CH_3$ | H | — |
| 2d | C | C | $CH_2O(CH_2)_2SiCH_3$ | H | H | $CH_3$ | H | — |
| 2e | C | C | $CH_2O(CH_2)_2SiCH_3$ | $CH_2O(CH_2)_2SiCH_3$ | H | $CH_3$ | H | — |
| 2f | C | C | $R^1$ and $R^2$ together are —$(CH_2)_6$— | | H | $CH_3$ | H | — |
| 2h | C | C | $R^1$ and $R^2$ together are —$(CH_2)_8$— | | H | $CH_3$ | H | — |
| 2i | C | C | $R^1$ and $R^2$ together are —$(CH_2)_9$— | | H | $CH_3$ | H | — |
| 2j | C | C | $R^1$ and $R^2$ together are —$(CH_2)_{10}$— | | H | $CH_3$ | H | — |

TABLE 3-continued

Preferred GSK-3 inhibitors

| Name | X | Y | R¹ | R² | R³ | R⁴ | R⁵ | R⁶/R⁷ |
|---|---|---|---|---|---|---|---|---|
| 2l | C | C | R¹ and R² together are —(CH₂CH₂O)₃(CH₂)₂— | | H | CH₃ | H | — |
| 2m | C | C | R¹ and R² together are —(CH₂CH₂O)₄(CH₂)₂— | | H | CH₃ | H | — |
| 3c | C | C | CH₃ | CH₃ | CH₃ | CH₃ | H | — |
| 3f | C | C | R¹ and R² together are —(CH₂)₆— | | CH₃ | CH₃ | H | — |
| 3g | C | C | R¹ and R² together are —(CH₂)₇— | | CH₃ | CH₃ | H | — |
| 3h | C | C | R¹ and R² together are —(CH₂)₈— | | CH₃ | CH₃ | H | — |
| 3i | C | C | R¹ and R² together are —(CH₂)₉— | | CH₃ | CH₃ | H | — |
| 3j | C | C | R¹ and R² together are —(CH₂)₁₀— | | CH₃ | CH₃ | H | — |
| 6a | C | C | H | H | H | CH₃ | Methoxy substituted CH₂aryl 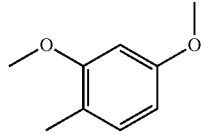 | — |
| 4a | C | N | H | H | H | H | H | — |
| 4c | C | N | CH₃ | CH₃ | H | H | H | — |
| 4e | C | N | CH₂O(CH₂)₂SiCH₃ | CH₂O(CH₂)₂SiCH₃ | H | H | H | — |
| 4h | C | N | R¹ and R² together are —(CH₂)₈— | | H | H | H | — |
| 4i | C | N | R¹ and R² together are —(CH₂)₉— | | H | H | H | — |
| 4j | C | N | R¹ and R² together are —(CH₂)₁₀— | | H | H | H | — |
| 4l | C | N | R¹ and R² together are —(CH₂CH₂O)₃(CH₂)₂— | | H | H | H | — |
| 4m | C | N | R¹ and R² together are —(CH₂CH₂O)₄(CH₂)₂— | | H | H | H | — |
| 5c | N | N | CH₃ | CH₃ | H | H | H | — |
| 5i | N | N | R¹ and R² together are —(CH₂)₉— | | H | H | H | — |
| 5m | N | N | R¹ and R² together are —(CH₂CH₂O)₄(CH₂)₂— | | H | H | H | — |
| 7a | N | C | H | H | H | H | Methoxy substituted CH₂aryl 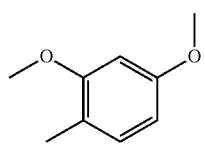 | — |
| 7d | N | C | CH₂O(CH₂)₂SiCH₃ | H | H | H | Methoxy substituted CH₂aryl 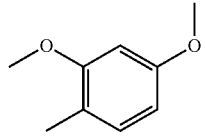 | — |
| 1n | C | C | R¹ and R² together are —(CH₂)₄CH(OR⁶)(CH₂)₄— | | H | H | H | Si$^t$BuPh₂ |
| 1o | C | C | R¹ and R² together are —(CH₂)₄CH(OR⁶)(CH₂)₄— | | H | H | H | H |
| 1p | C | C | R¹ and R² together are —(CH₂)₄CH(OR⁶)(CH₂)₄— | | H | H | H | CH₂CH=CH₂ |
| 8o | C | C | R¹ and R² together are —(CH₂)₄CH(OR⁶)(CH₂)₄— | | H | H | CH₂Ph | H |
| 1q | C | C | R¹ and R² together are —(CH₂)₃CH(OR⁶)(CH₂)₅— | | H | H | H | CH₂CH=CH₂ |
| 1r | C | C | R¹ and R² together are —(CH₂)₂CH(OR⁶)(CH₂)₆— | | H | H | H | CH₂CH=CH₂ |
| 1s | C | C | R¹ and R² together are —CH(R⁷)(CH₂)₈— | | H | H | H | CH₂OCH₂CH=CH₂ |
| 1t | C | C | R¹ and R² together are —CH(R⁷)(CH₂)₈— | | H | H | H | (CH₂)₂CH=CH₂ |

The use of small molecule inhibitors represents a powerful approach to direct differentiation of embryonic stem cells (ESCs) towards a specific cell type. Generation of cells characteristic of the definitive endoderm (DE), from which the liver and pancreas develop, is an attractive target for chemically-directed differentiation. In particular, the ability to generate hepatocytes is not only of interest in regenerative medicine but also provides a novel platform for drug toxicity screening. It has now been demonstrated that treatment with GSK-3 inhibitors promotes differentiation of human ESCs towards the DE, with prolonged treatment resulting in generation of a population of cells displaying hepatoblast characteristics. In turn, these cells have the ability to progress to a more mature hepatocyte phenotype under defined culture conditions.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications are covered by the appended claims.

The content of all references cited herein are incorporated herein by reference in their entirety.

References

Agarwal, S., Holton, K. L., and Lanza, R. (2008). Efficient differentiation of functional hepatocytes from human embryonic stem cells. Stem Cells 26, 1117-1127.

Bone, H. K., Damiano, T., Bartlett, S., Perry, A., Letchford, J., Ripoll, Y. S., Nelson, A. S., and Welham, M. J. (2009). Involvement of GSK-3 in regulation of murine embryonic stem cell self-renewal revealed by a series of bisindolylmaleimides. Chem Biol 16, 15-27.

Collingnon, J., Varlet, I., and Robertson, E. J. (1996) Relationship between asymmetric nodal expression and the direction of embryonic turning. Nature 381, 155-158

D'Amour, K. A., Agulnick, A. D., Eliazer, S., Kelly, O. G., Kroon, E., and Baetge, E. E. (2005). Efficient differentiation of human embryonic stem cells to definitive endoderm. Nat Biotechnol 23, 1534-1541.

D'Amour, K. A., Bang, A. G., Eliazer, S., Kelly, O. G., Agulnick, A. D., Smart, N. G., Moorman, M. A., Kroon, E., Carpenter, M. K., and Baetge, E. E. (2006). Production of pancreatic hormone-expressing endocrine cells from human embryonic stem cells. Nat Biotechnol 24, 1392-1401.

Gouon-Evans, V., Boussemart, L., Gadue, P., Nierhoff, D., Koehler, C. I., Kubo, A., Shafritz, D. A., and Keller, G. (2006). BMP-4 is required for hepatic specification of mouse embryonic stem cell-derived definitive endoderm. Nat Biotechnol 24, 1402-1411.

McGrath, K. E., Koniski, A. D., Maltby, K. M., McGann, J. K., and Palis, J. (1999). Embryonic expression and function of the chemokine SDF-1 and its receptor, CXCR4. Dev Biol 213, 442-456.

Tada, S., Era, T., Furusawa, C., Sakurai, H., Nishikawa, S., Kinoshita, M., Nakao, K., and Chiba, T. (2005). Characterization of mesendoderm: a diverging point of the definitive endoderm and mesoderm in embryonic stem cell differentiation culture. Development 132, 4363-4374.

Takahashi K, Tanabe K, Ohnuki M, Narita M, Ichisaka T, Tomoda K and Yamanaka S (2007). Induction of pluripotent stem cells from adult human fibroblasts by defined factors. Cell. November 30; 131(5) 861-72

Takenaga, M., Fukumoto, M., and Hori, Y. (2007). Regulated Nodal signaling promotes differentiation of the definitive endoderm and mesoderm from ES cells. J Cell Sci 120, 2078-2090.

Welham, M. J., Duronio, V., Leslie, K. B., Bowtell, D., and Schrader, J. W. (1994). Multiple hemopoietins, with the exception of interleukin-4, induce modification of She and mSos 1, but not their translocation. J Biol Chem 269, 21165-21176.

Yasunaga, M., Tada, S., Torikai-Nishikawa, S., Nakano, Y., Okada, M., Jakt, L. M., Nishikawa, S., Chiba, T., and Era, T. (2005). Induction and monitoring of definitive and visceral endoderm differentiation of mouse ES cells. Nat Biotechnol 23, 1542-1550.

The invention claimed is:

1. An in vitro method for inducing differentiation of a human embryonic stem cell or a population of human embryonic stem cells into a hepatocyte-like cell or a population of hepatocyte-like cells comprising incubating the human embryonic stem cells or the population of human embryonic stem cells with a GSK-3 inhibitor, thereby inducing the differentiation of the human embryonic stem cell or the population of human embryonic stem cells into a hepatocyte-like cell or a population of hepatocyte-like cells, wherein the hepatocyte-like cell or the population of hepatocyte-like cells differentiated from the human embryonic stem cell or the population of human embryonic stem cells are positive for hepatocyte markers HNF4α, AFP, albumin, and transthyretin.

2. The method of claim 1, wherein the GSK-3 inhibitor is a compound of Formula (A):

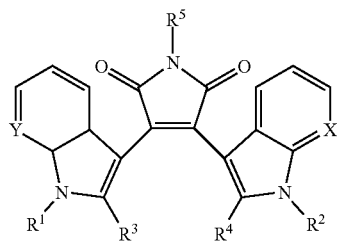

(A)

wherein:
$R^1$ and $R^2$ are each independently H, a $C_1$-$C_6$ alkyl, or $CH_2O(CH_2)_2SiCH_3$, or $R^1$ and $R^2$ together are —$(CH_2)_n$— unsubstituted or substituted by $OR^6$ or $R^7$, or —$(CH_2CH_2O)_m(CH_2)_2$—;

$R^3$ is H or a $C_1$-$C_6$ alkyl;

$R^4$ is H or a $C_1$-$C_6$ alkyl;

$R^5$ is H or $CH_2$aryl, wherein aryl is unsubstituted or substituted by alkoxy;

$R^6$ is H, $CH_2CH=CH_2$, $CH_2CH_2CH=CH_2$, $CH_2OCH_2CH=CH_2$ or $Si^tBuPh_2$;

$R^7$ is H, $CH_2CH=CH_2$, $CH_2CH_2CH=CH_2$, $CH_2OCH_2CH=CH_2$ or $Si^tBuPh_2$;

n is 6, 7, 8, 9, 10, or 11;

m is 3 or 4; and

X and Y are each independently C or N.

3. The method of claim 2, wherein $R^1$, $R^2$, $R^3$, or $R^4$, is $CH_3$.

4. The method of claim 2, wherein $R^5$ is methoxy.

5. The method of claim 2, wherein the GSK-3 inhibitor is selected from a compound having one of the following structures:

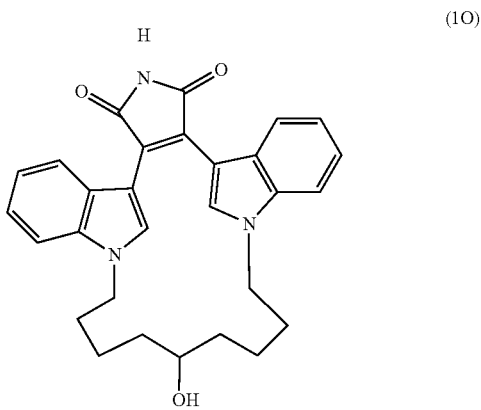

(1O)

-continued
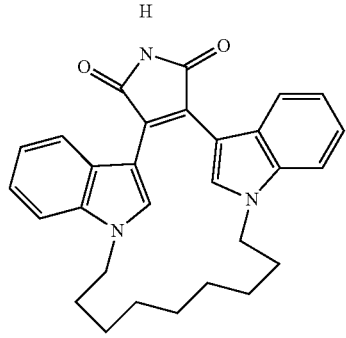
(1I)
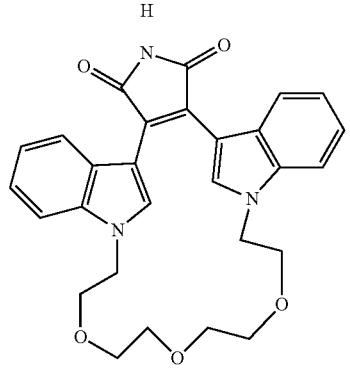
(1L)
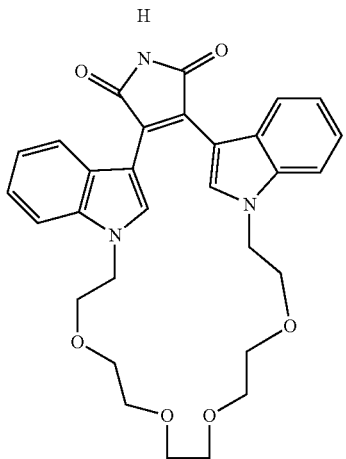
(1M)
-continued
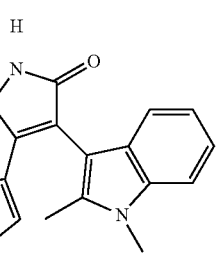
(2C)
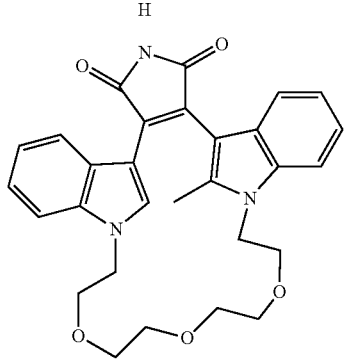
(2L)
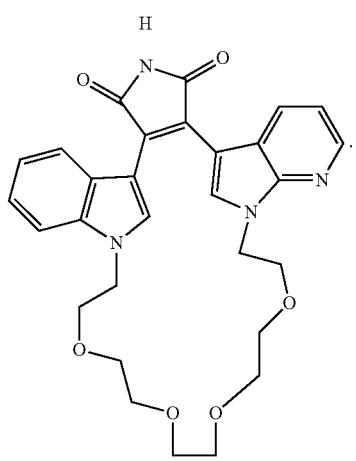
(4M)
* * * * *

```
                        SEQUENCE LISTING

<160> NUMBER OF SEQ ID NOS: 32

<210> SEQ ID NO 1
<211> LENGTH: 21
<212> TYPE: DNA
<213> ORGANISM: Artificial Sequence
<220> FEATURE:
<223> OTHER INFORMATION: PCR Primer

<400> SEQUENCE: 1
gagatgtgct ggattgtctg c                                             21

<210> SEQ ID NO 2
<211> LENGTH: 21
<212> TYPE: DNA
<213> ORGANISM: Artificial Sequence
<220> FEATURE:
<223> OTHER INFORMATION: PCR Primer

<400> SEQUENCE: 2
taactcctgg tatcctttag c                                             21

<210> SEQ ID NO 3
<211> LENGTH: 26
<212> TYPE: DNA
<213> ORGANISM: Artificial Sequence
<220> FEATURE:
<223> OTHER INFORMATION: PCR Primer

<400> SEQUENCE: 3
cctttggcac aatgaagtgg gtaacc                                        26

<210> SEQ ID NO 4
```

```
<211> LENGTH: 25
<212> TYPE: DNA
<213> ORGANISM: Artificial Sequence
<220> FEATURE:
<223> OTHER INFORMATION: PCR Primer

<400> SEQUENCE: 4
cagcagtcag ccatttcacc atagg                                             25

<210> SEQ ID NO 5
<211> LENGTH: 22
<212> TYPE: DNA
<213> ORGANISM: Artificial Sequence
<220> FEATURE:
<223> OTHER INFORMATION: PCR Primer

<400> SEQUENCE: 5
gccctctccc tccctccac gc                                                 22

<210> SEQ ID NO 6
<211> LENGTH: 21
<212> TYPE: DNA
<213> ORGANISM: Artificial Sequence
<220> FEATURE:
<223> OTHER INFORMATION: PCT Primer

<400> SEQUENCE: 6
ccgttgctca cagaccacag g                                                 21

<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7
gacagtgccc ttcagccag                                                    19

<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8
gttcagtgca gttcagtgg                                                    19

<210> SEQ ID NO 9
<211> LENGTH: 19
<212> TYPE: DNA
<213> ORGANISM: Artificial Sequence
<220> FEATURE:
<223> OTHER INFORMATION: PCR Primer

<400> SEQUENCE: 9
ccgcatctgg agaaccagc                                                    19

<210> SEQ ID NO 10
<211> LENGTH: 21
<212> TYPE: DNA
<213> ORGANISM: Artificial Sequence
<220> FEATURE:
<223> OTHER INFORMATION: PCR Primer

<400> SEQUENCE: 10
```

-continued

```
ggtgcagcct gtacttgtcc g                                              21

<210> SEQ ID NO 11
<211> LENGTH: 18
<212> TYPE: DNA
<213> ORGANISM: Artificial Sequence
<220> FEATURE:
<223> OTHER INFORMATION: PCR Primer

<400> SEQUENCE: 11
agatggaagg gcacgagc                                                  18

<210> SEQ ID NO 12
<211> LENGTH: 18
<212> TYPE: DNA
<213> ORGANISM: Artificial Sequence
<220> FEATURE:
<223> OTHER INFORMATION: PCR Primer

<400> SEQUENCE: 12
caggccggcg ttgatgtt                                                  18

<210> SEQ ID NO 13
<211> LENGTH: 21
<212> TYPE: DNA
<213> ORGANISM: Artificial Sequence
<220> FEATURE:
<223> OTHER INFORMATION: PCR Primer

<400> SEQUENCE: 13
agcagtgctc ctgcgtcccg a                                              21

<210> SEQ ID NO 14
<211> LENGTH: 21
<212> TYPE: DNA
<213> ORGANISM: Artificial Sequence
<220> FEATURE:
<223> OTHER INFORMATION: PCR Primer

<400> SEQUENCE: 14
ctctgatgag gaccgcttct g                                              21

<210> SEQ ID NO 15
<211> LENGTH: 21
<212> TYPE: DNA
<213> ORGANISM: Artificial Sequence
<220> FEATURE:
<223> OTHER INFORMATION: PCR Primer

<400> SEQUENCE: 15
tggcgagcac ctgctgctcg g                                              21

<210> SEQ ID NO 16
<211> LENGTH: 21
<212> TYPE: DNA
<213> ORGANISM: Artificial Sequence
<220> FEATURE:
<223> OTHER INFORMATION: PCR Primer

<400> SEQUENCE: 16
atctgccacg tgatgctctg c                                              21

<210> SEQ ID NO 17
<211> LENGTH: 19
<212> TYPE: DNA
```

```
<213> ORGANISM: Artificial Sequence
<220> FEATURE:
<223> OTHER INFORMATION: PCR Primer

<400> SEQUENCE: 17
taccccgaca tccacttgc                                                  19

<210> SEQ ID NO 18
<211> LENGTH: 19
<212> TYPE: DNA
<213> ORGANISM: Artificial Sequence
<220> FEATURE:
<223> OTHER INFORMATION: PCR Primer

<400> SEQUENCE: 18
caggcagttc acatctacc                                                  19

<210> SEQ ID NO 19
<211> LENGTH: 21
<212> TYPE: DNA
<213> ORGANISM: Artificial Sequence
<220> FEATURE:
<223> OTHER INFORMATION: PCR Primer

<400> SEQUENCE: 19
cctgattctt ccaccagtcc c                                               21

<210> SEQ ID NO 20
<211> LENGTH: 21
<212> TYPE: DNA
<213> ORGANISM: Artificial Sequence
<220> FEATURE:
<223> OTHER INFORMATION: PCR Primer

<400> SEQUENCE: 20
gtcgggttca ccaggcatcc c                                               21

<210> SEQ ID NO 21
<211> LENGTH: 19
<212> TYPE: DNA
<213> ORGANISM: Artificial Sequence
<220> FEATURE:
<223> OTHER INFORMATION: PCR Primer

<400> SEQUENCE: 21
ccgagggcag acatcatcc                                                  19

<210> SEQ ID NO 22
<211> LENGTH: 19
<212> TYPE: DNA
<213> ORGANISM: Artificial Sequence
<220> FEATURE:
<223> OTHER INFORMATION: PCR Primer

<400> SEQUENCE: 22
taggtccatc tgaaaccgc                                                  19

<210> SEQ ID NO 23
<211> LENGTH: 21
<212> TYPE: DNA
<213> ORGANISM: Artificial Sequence
<220> FEATURE:
<223> OTHER INFORMATION: PCR Primer

<400> SEQUENCE: 23
tgagggtgaa gcaggagtcg g                                               21
```

```
<210> SEQ ID NO 24
<211> LENGTH: 21
<212> TYPE: DNA
<213> ORGANISM: Artificial Sequence
<220> FEATURE:
<223> OTHER INFORMATION: PCR Primer

<400> SEQUENCE: 24
aagattttca ttgttgtcag c                                              21

<210> SEQ ID NO 25
<211> LENGTH: 21
<212> TYPE: DNA
<213> ORGANISM: Artificial Sequence
<220> FEATURE:
<223> OTHER INFORMATION: PCR Primer

<400> SEQUENCE: 25
tcatggtgtg ggctaaggac g                                              21

<210> SEQ ID NO 26
<211> LENGTH: 21
<212> TYPE: DNA
<213> ORGANISM: Artificial Sequence
<220> FEATURE:
<223> OTHER INFORMATION: PCR Primer

<400> SEQUENCE: 26
cggtacttgt agttggggtg g                                              21

<210> SEQ ID NO 27
<211> LENGTH: 20
<212> TYPE: DNA
<213> ORGANISM: Artificial Sequence
<220> FEATURE:
<223> OTHER INFORMATION: PCR Primer

<400> SEQUENCE: 27
agaagggaga tgtggccttt                                                20

<210> SEQ ID NO 28
<211> LENGTH: 20
<212> TYPE: DNA
<213> ORGANISM: Artificial Sequence
<220> FEATURE:
<223> OTHER INFORMATION: PCR Primer

<400> SEQUENCE: 28
cgaccggaac aaacaaaact                                                20

<210> SEQ ID NO 29
<211> LENGTH: 20
<212> TYPE: DNA
<213> ORGANISM: Artificial Sequence
<220> FEATURE:
<223> OTHER INFORMATION: PCR Primer

<400> SEQUENCE: 29
ccactcattc ttggcaggct                                                20

<210> SEQ ID NO 30
<211> LENGTH: 20
<212> TYPE: DNA
<213> ORGANISM: Artificial Sequence
<220> FEATURE:
```

```
<223> OTHER INFORMATION: PCR Primer

<400> SEQUENCE: 30
aggtgtcatc agcagccttt                                              20

<210> SEQ ID NO 31
<211> LENGTH: 20
<212> TYPE: DNA
<213> ORGANISM: Artificial Sequence
<220> FEATURE:
<223> OTHER INFORMATION: PCR Primer

<400> SEQUENCE: 31
taggcaccag ggtgtgatgg                                              20

<210> SEQ ID NO 32
<211> LENGTH: 20
<212> TYPE: DNA
<213> ORGANISM: Artificial Sequence
<220> FEATURE:
<223> OTHER INFORMATION: PCR Primer

<400> SEQUENCE: 32
catggctggg gtgttgaagg                                              20
```